US009278229B1

(12) United States Patent
Reinke et al.

(10) Patent No.: US 9,278,229 B1
(45) Date of Patent: Mar. 8, 2016

(54) ANTI-TACHYARRHYTHMIA SHOCK DETECTION

(71) Applicant: Medtronic, Inc., Minneapolis, MN (US)

(72) Inventors: James D. Reinke, Maple Grove, MN (US); Glenn M. Roline, Anoka, MN (US); Shohan T. Hossain, Maple Grove, MN (US); Michael W. Heinks, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/603,631

(22) Filed: Jan. 23, 2015

(51) Int. Cl.
*A61N 1/00* (2006.01)
*A61N 1/39* (2006.01)
*A61N 1/362* (2006.01)
*A61N 1/37* (2006.01)

(52) U.S. Cl.
CPC ............ *A61N 1/3937* (2013.01); *A61N 1/3621* (2013.01); *A61N 1/37* (2013.01)

(58) Field of Classification Search
CPC ......... A61N 1/36135–1/36142; A61N 1/3925; A61N 1/3956; A61N 1/36153; A61N 1/3621; A61N 1/3937; A61N 1/37; A61N 1/3962
See application file for complete search history.

(56) References Cited

U.S. PATENT DOCUMENTS

| 5,117,824 | A | 6/1992 | Keimel et al. |
| 5,545,186 | A | 8/1996 | Olson et al. |
| 5,741,312 | A | 4/1998 | Vonk et al. |
| 5,755,736 | A | 5/1998 | Gillberg et al. |
| 5,772,692 | A | 6/1998 | Armstrong |
| 6,421,563 | B1 | 7/2002 | Sullivan et al. |
| 6,618,619 | B1 | 9/2003 | Florio et al. |
| 6,892,094 | B2 | 5/2005 | Ousdigian et al. |
| 7,162,298 | B2 | 1/2007 | Idekar et al. |
| 7,761,150 | B2 | 7/2010 | Ghanem et al. |
| 8,744,572 | B1 | 6/2014 | Greenhut et al. |
| 8,923,963 | B2 | 12/2014 | Bonner et al. |
| 2010/0069986 | A1 | 3/2010 | Stahl et al. |
| 2014/0121720 | A1 | 5/2014 | Bonner et al. |

OTHER PUBLICATIONS

Kruse, et al., "Detecting and Distinguishing Cardiac Pacing Artifacts," Analog Dialogue 46-11, Nov. 2012, 6 pages.

*Primary Examiner* — Scott Getzow
(74) *Attorney, Agent, or Firm* — Michael J. Ostrom

(57) ABSTRACT

An implantable pacemaker detects delivery of an anti-tachyarrhythmia shock by another device. The implantable pacemaker delivers cardiac stimulation therapy within a patient. The implantable pacemaker senses, via the electrode pair, an electrical signal. The implantable pacemaker detects the anti-tachyarrhythmia shock based on the sensed electrical signal by detecting DC voltage polarization across the electrode pair within the patient. The implantable pacemaker alters the cardiac stimulation therapy based on the detected anti-tachyarrhythmia shock.

20 Claims, 13 Drawing Sheets

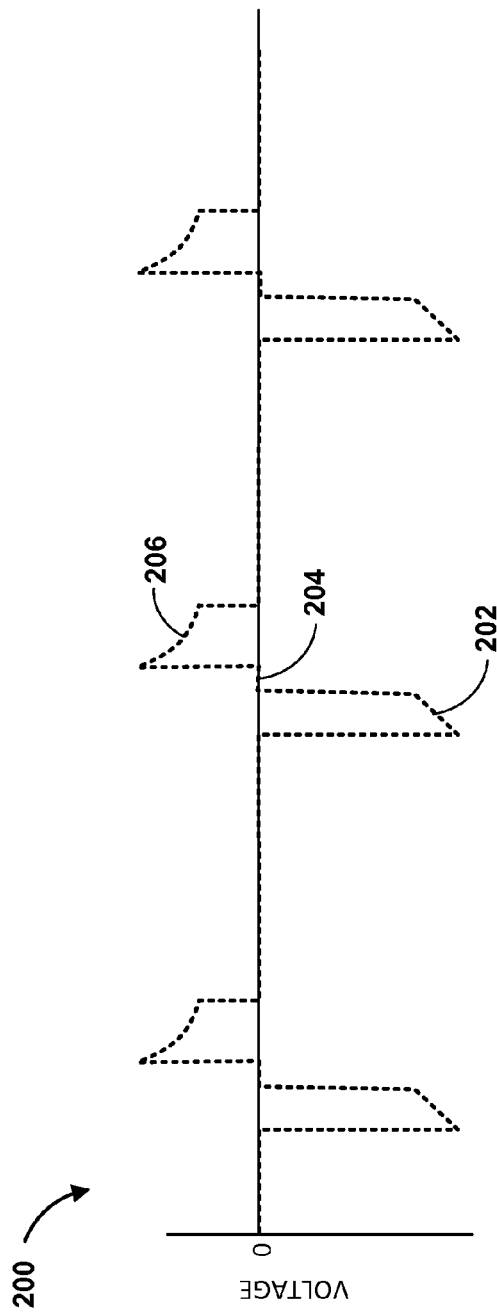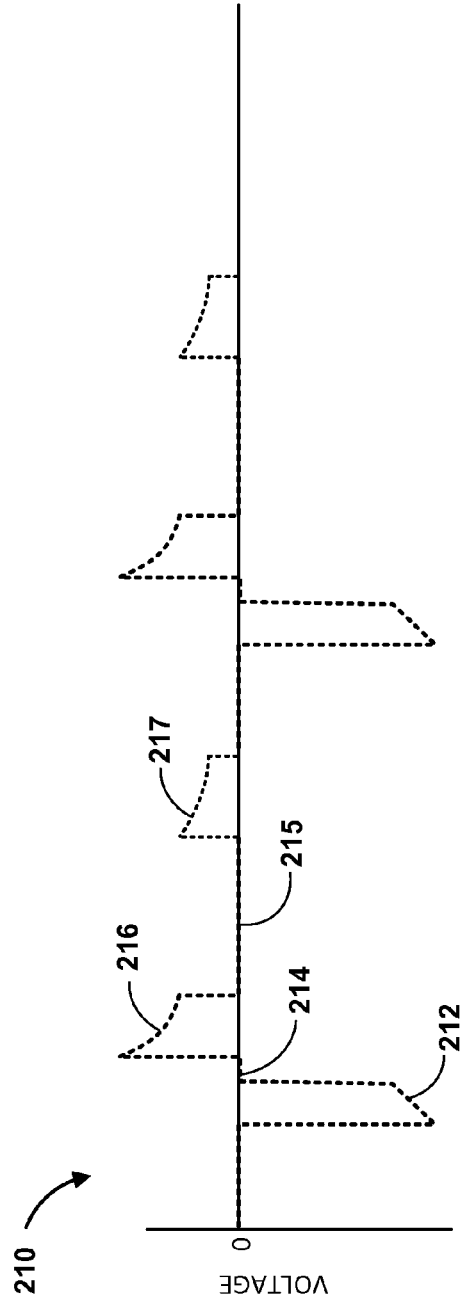

ANTI-TACHYARRHYTHMIA SHOCK DETECTION

TECHNICAL FIELD

The invention relates to medical devices, and, more particularly, to implantable medical devices configured to detect and treat cardiac arrhythmias.

BACKGROUND

Implantable cardioverter defibrillators (ICDs) and implantable artificial pacemakers may provide cardiac pacing therapy to a patient's heart when the natural pacemaker and/or conduction system of the heart fails to provide synchronized atrial and ventricular contractions at rates and intervals sufficient to sustain healthy patient function. Such antibradycardial pacing may provide relief from symptoms, or even life support, for a patient. Cardiac pacing may also provide electrical overdrive stimulation, e.g., anti-tachyarrhythmia pacing (ATP) therapy, to suppress or convert tachyarrhythmias, again supplying relief from symptoms and preventing or terminating arrhythmias that could lead to sudden cardiac death.

Cardiac pacing by conventional pacemakers and/or ICDs is usually provided by a pulse generator implanted subcutaneously or sub-muscularly in or near a pectoral region of a patient. The generator typically connects to the proximal end of one or more implanted leads, the distal end of which contains one or more electrodes for positioning adjacent to the inside or outside wall of a cardiac chamber. Each of the leads may be secured near or against the cardiac tissue to provide sufficient transmission of electrical energy to the cardiac tissue in order to capture the heart.

ICDs may also be used to deliver high-energy cardioversion or defibrillation pulses to a patient's heart when atrial or ventricular fibrillation is detected. Cardioversion shocks are typically delivered in synchrony with a detected R-wave when fibrillation detection criteria are met. Defibrillation pulses are typically delivered when fibrillation criteria are met, and the R-wave cannot be discerned from signals sensed by the ICD.

Currently, ICDs use endocardial or epicardial leads which extend from the ICD housing through the venous system into the heart. Electrodes positioned in or adjacent to the heart by the leads are used for pacing and sensing functions. Cardioversion and defibrillation pulses (e.g., anti-tachyarrhythmia shocks) are generally applied between a coil electrode carried by one of the leads and the ICD housing, which acts as an active can electrode.

SUMMARY

Artificial pacemakers may adjust cardiac therapy based on the application of defibrillation and/or cardioversion therapy, such as defibrillation and/or cardioversion therapy from an automated external defibrillator (AED) or a subcutaneous ICD. In situations in which a subcutaneous ICD operates in conjunction with a co-implanted artificial pacemaker, such as a leadless pacing device (LPD), it may be important that the pacemaker knows when the subcutaneous ICD has delivered a shock. Based on the knowledge that the shock has been delivered, the pacemaker may, for example, terminate ATP and/or activate post-shock pacing. This disclosure describes the implementation of an anti-tachyarrhythmia shock detector based on the detection of the signal across an electrode pair of the LPD or other pacemaker. A number of additional uses for the detector are also described.

This disclosure includes at least three general techniques for detection of an anti-tachyarrhythmia shock: detection of the relatively high amplitude level of an anti-tachyarrhythmia shock, detection of a high slew rate of the leading and trailing edges, and detection of a large post-shock polarization change. Each technique looks for a different electrical signal characteristic. Any of the three techniques may be combined to improve sensitivity and/or specificity. For example, an implantable pacing device may combine detection of the high level of an anti-tachyarrhythmia shock combined with one or both of the detection of a high slew rate of the leading and trailing edges, and the detection of a large post-shock polarization change.

In one example, this disclosure is directed to a method for detecting, with an implantable pacemaker, delivery of an anti-tachyarrhythmia shock by another device. The method comprises delivering, by the implantable pacemaker, cardiac stimulation therapy, sensing, by the implantable pacemaker via an electrode pair within the patient, an electrical signal, detecting, by the implantable pacemaker, the anti-tachyarrhythmia shock based on the sensed electrical signal by detecting DC voltage polarization across the electrode pair within the patient, and altering the cardiac stimulation therapy delivered by the implantable pacemaker based on the detected anti-tachyarrhythmia shock.

In another example, this disclosure is directed to an implantable pacing device comprising an electrode pair, a signal generator configured to deliver cardiac stimulation therapy to a heart of a patient, a shock detector configured to sense, from the electrode pair when the implantable medical device is implanted within a patient, an electrical signal, and a processor configured to detect an anti-tachyarrhythmia shock based on the sensed electrical signal by detecting DC voltage polarization across the electrode pair within the patient, and alter the cardiac stimulation therapy based on the detected anti-tachyarrhythmia shock.

In a further example, this disclosure is directed to a system comprising a subcutaneous implantable cardioverter defibrillator comprising a first set of electrodes and configured to sense a first electrical signal from a heart of a patient via the one or more first electrodes, detect a tachyarrhythmia within the sensed first electrical signal, and determine, based on the detected tachyarrhythmia, to deliver anti-tachyarrhythmia shock therapy to the patient to treat the detected arrhythmia. The system further includes a leadless pacing device configured to be implanted within the heart of the patient. The leadless pacing device comprises a second set of electrodes, a signal generator configured to deliver stimulation therapy to the heart of the patient, a shock detector configured to sense, from the second set of electrodes when the leadless pacing device is implanted within a patient, an electrical signal, and a processor configured to detect an anti-tachyarrhythmia shock based on the sensed electrical signal by detecting DC voltage polarization across the second set of electrodes within the patient, and alter the cardiac stimulation therapy based on the detected anti-tachyarrhythmia shock.

The details of one or more examples are set forth in the accompanying drawings and the description below. Other features, objects, and advantages will be apparent from the description and drawings, and from the claims.

BRIEF DESCRIPTION OF DRAWINGS

FIG. 6A is a functional block diagram illustrating an example of an anti-tachyarrhythmia shock signal edge detector, whereas

FIG. 7A is a functional block diagram illustrating an example of an anti-tachyarrhythmia shock amplitude detector, whereas

FIG. 10 illustrates an example waveform of biphasic cardiac pacing including a pacing pulse having two windows separated by a period of substantially no stimulation, the period of no stimulation being suitable for sensing electrical signals, including electrical signals indicative of an anti-tachyarrhythmia shock.

FIG. 11 illustrates an example waveform of biphasic cardiac pacing including a pacing pulse having three pacing windows separated by two periods of substantially no stimulation, the periods of no stimulation being suitable for sensing electrical signals, including electrical signals indicative of an anti-tachyarrhythmia shock.

DETAILED DESCRIPTION

Figure 1:
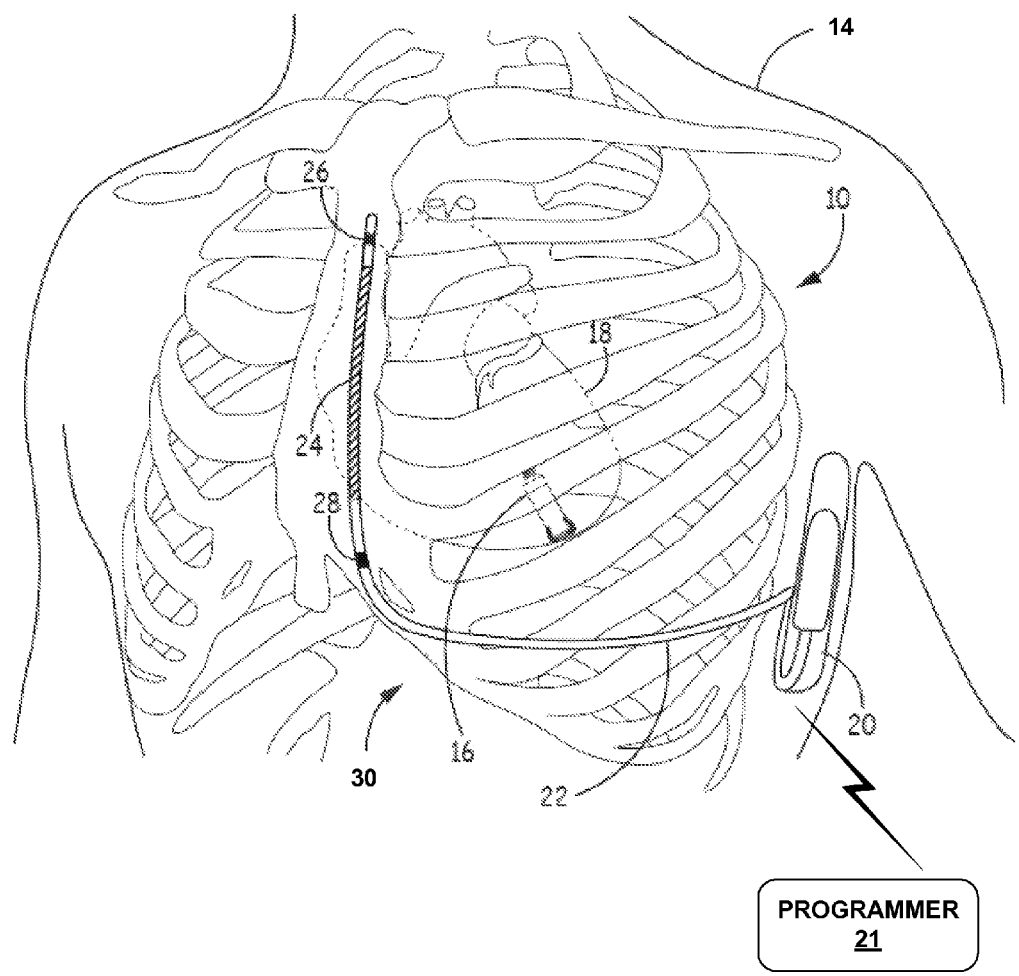
FIG. 1 is a conceptual drawing illustrating an example system that includes a subcutaneous implantable cardioverter defibrillator (ICD) implanted exterior to the rib cage of a patient and a leadless pacing device (LPD) implanted within a cardiac chamber of the patient.

FIG. 1 is a conceptual drawing illustrating an example cardiac system 10 implanted within a patient 14. Cardiac system 10 includes a subcutaneous ICD system 30 implanted above the ribcage and sternum and a leadless cardiac pacing device (LPD) 16 implanted within a heart 18 of patient 14.

Subcutaneous ICD system 30 includes an implantable cardiac defibrillator (ICD) 20 connected to at least one implantable cardiac defibrillation lead 22. ICD 20 is configured to deliver high-energy cardioversion or defibrillation pulses to a patient's heart when atrial or ventricular fibrillation is detected. Cardioversion shocks are typically delivered in synchrony with a detected R-wave when fibrillation detection criteria are met. Defibrillation pulses are typically delivered when fibrillation criteria are met, and the R-wave cannot be discerned from signals sensed by ICD 20.

ICD 20 of FIG. 1 is implanted subcutaneously on the left side of patient 14 above the ribcage. Defibrillation lead 22 extends subcutaneously above the ribcage from ICD 20 toward a center of the torso of patient 14, bends or turns near the center of the torso, and extends subcutaneously superior above the ribcage and/or sternum. Defibrillation lead 22 may be offset laterally to the left or the right of the sternum or located over the sternum. Defibrillation lead 22 may extend substantially parallel to the sternum or be angled lateral from the sternum at either the proximal or distal end.

In other instances, lead 22 may be implanted at other extravascular locations. For example, lead 22 may be implanted at least partially in a substernal location, e.g., between the ribcage and/or sternum and heart. In one such configuration, a proximal portion of lead 22 extends subcutaneously from ICD 20 toward the sternum and a distal portion of lead 22 extends superior under or below the sternum in the anterior mediastinum. The anterior mediastinum is bounded laterally by the pleurae, posteriorly by the pericardium, and anteriorly by the sternum. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 22 extends along the posterior side of the sternum substantially within the loose connective tissue and/or substernal musculature of the anterior mediastinum. Lead 22 may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum or ribcage.

Defibrillation lead 22 includes an insulative lead body having a proximal end that includes a connector configured to be connected to ICD 20 and a distal portion that includes one or more electrodes. Defibrillation lead 22 also includes one or more conductors that form an electrically conductive path within the lead body and interconnect the electrical connector and respective ones of the electrodes.

Defibrillation lead 22 includes a defibrillation electrode 24 toward the distal portion of defibrillation lead 22, e.g., toward the portion of defibrillation lead 22 extending along the sternum. Defibrillation lead 22 is placed along sternum such that a therapy vector between defibrillation electrode 24 and a housing electrode formed by or on ICD 20 (or other second electrode of the therapy vector) is substantially across a ventricle of heart 18. The therapy vector may, in one example, be viewed as a line that extends from a point on defibrillation electrode 24 (e.g., a center of the defibrillation electrode 24)

to a point on the housing electrode of ICD 20. Defibrillation electrode 24 may, in one example, be an elongated coil electrode.

Defibrillation lead 22 may also include one or more sensing electrodes, such as sensing electrodes 26 and 28, located along the distal portion of defibrillation lead 22. In the example illustrated in FIG. 1, sensing electrodes 26 and 28 are separated from one another by defibrillation electrode 24. In other examples, however, sensing electrodes 26 and 28 may be both distal of defibrillation electrode 24 or both proximal of defibrillation electrode 24. In other examples, lead 22 may include more or fewer electrodes at various locations proximal and/or distal to defibrillation electrode 24. In the same or different examples, ICD 20 may include one or more electrodes on another lead (not shown).

ICD system 30 may sense electrical signals via one or more sensing vectors that include combinations of electrodes 26 and 28 and the housing electrode of ICD 20. For example, ICD 20 may obtain electrical signals sensed using a sensing vector between electrodes 26 and 28, obtain electrical signals sensed using a sensing vector between electrode 26 and the conductive housing electrode of ICD 20, obtain electrical signals sensed using a sensing vector between electrode 28 and the conductive housing electrode of ICD 20, or a combination thereof. In some instances, ICD 20 may even sense cardiac electrical signals using a sensing vector that includes defibrillation electrode 24 and one of sensing electrodes 26 and 28 or the housing electrode of ICD 20.

The sensed electrical intrinsic signals may include electrical signals generated by cardiac muscle and indicative of depolarizations and repolarizations of heart 18 at various times during the cardiac cycle. Additionally, the sensed electrical signals may also include electrical signals, e.g., pacing pulses, generated and delivered to heart 18 by LPD 16. ICD 20 analyzes the electrical signals sensed by the one or more sensing vectors to detect tachyarrhythmia, such as ventricular tachycardia or ventricular fibrillation. In response to detecting the tachycardia, ICD 20 may begin to charge a storage element, such as a bank of one or more capacitors, and, when charged, deliver one or more defibrillation pulses via defibrillation electrode 24 of defibrillation lead 22 if the tachyarrhythmia is still present.

In the example of FIG. 1, LPD 16 is implanted within right ventricle of heart 18 to sense electrical activity of heart 18 and deliver pacing therapy, e.g., anti-tachycardia pacing (ATP) therapy, bradycardia pacing therapy, and/or post-shock pacing, to heart 18. LPD 16 may be attached to an interior wall of the right ventricle of heart 18 via one or more fixation elements that penetrate the tissue. These fixation elements may secure LPD 16 to the cardiac tissue and retain an electrode (e.g., a cathode or an anode) in contact with the cardiac tissue. However, in other examples, system 10 may include additional pacing devices 16 within respective chambers of heart 18 (e.g., right or left atrium and/or left ventricle). In further examples, LPD 16 may be attached to an external surface of heart 18 (e.g., in contact with the epicardium) such that LPD 16 is disposed outside of heart 18.

LPD 16 may be capable sensing electrical signals using the electrodes carried on the housing of LPD 16. These electrical signals may be electrical signals generated by cardiac muscle and indicative of depolarizations and repolarizations of heart 18 at various times during the cardiac cycle. LPD 16 may analyze the sensed electrical signals to detect tachyarrhythmias, such as ventricular tachycardia or ventricular fibrillation. In response to detecting the tachyarrhythmia, LPD 16 may, e.g., depending on the type of tachyarrhythmia, begin to deliver ATP therapy via the electrodes of LPD 16. In addition to or instead of ATP therapy, LPD 16 may also deliver bradycardia pacing therapy and post-shock pacing.

Cardiac LPD 16 and subcutaneous ICD system 30 may be configured to operate completely independent of one another. In such a case, LPD 16 and subcutaneous ICD system 30 are not capable of establishing telemetry communication sessions with one another to exchange information about sensing and/or therapy using one-way or two-way communication. Instead, each of LPD 16 and subcutaneous ICD system 30 analyze the data sensed via their respective electrodes to make tachyarrhythmia detection and/or therapy decisions. As such, each device does not know if the other will detect the tachyarrhythmia, if or when it will provide therapy, and the like.

During a tachyarrhythmia that could be treated with either ATP or a defibrillation pulse, it is important to ensure that ATP therapies do not overlap or take place after the defibrillation pulse. Applying ATP after a defibrillation pulse could be pro-arrhythmic and present a hazard to the patient. Moreover, it would be desirable for LPD 16 to deliver post-shock pacing after delivery of a cardioversion/defibrillation pulse. Systems could be designed to provide device-to-device communication between subcutaneous ICD system 30 and LPD 16, but this may add complexity to the system and not be highly effective or fast enough to prevent unwanted ATP therapies post defibrillation pulse or too slow to initiate post-shock pacing therapies. The shock detection techniques described herein, however, improve the coordination of therapy between subcutaneous ICD 20 and LPD 16 without requiring device-to-device communication.

Although FIG. 1 is described in the context of a subcutaneous ICD system 30 and a LPD 16, the techniques may be applicable to other coexistent systems. For example, an ICD system that includes a lead having a distal portion that is implanted at least partially under the sternum (or other extrapericardial location) instead of being implanted above the ribs and/or sternum. As another example, instead of a leadless pacing device, a pacing system may be implanted having a pacemaker and one or more leads connected to and extending from the pacemaker into one or more chambers of the heart or attached to the outside of the heart to provide pacing therapy to the one or more chambers. As such, the example of FIG. 1 is illustrated for exemplary purposes only and should not be considered limiting of the techniques described herein.

External programmer 21 may be configured to communicate with one or both of subcutaneous ICD system 30 and LPD 16. In examples where external programmer 21 only communicates with one of subcutaneous ICD system 30 and LPD 16, the non-communicative device may receive instructions from or transmit data to the device in communication with programmer 21. In some examples, programmer 21 comprises a handheld computing device, computer workstation, or networked computing device. Programmer 21 may include a user interface that receives input from a user. In other examples, the user may also interact with programmer 21 remotely via a networked computing device. The user may interact with programmer 21 to communicate with LPD 16 and/or subcutaneous ICD system 30. For example, the user may interact with programmer 21 to send an interrogation request and retrieve therapy delivery data, update therapy parameters that define therapy, manage communication between LPD 16 and/or subcutaneous ICD system 30, or perform any other activities with respect to LPD 16 and/or subcutaneous ICD system 30. Although the user is a physician, technician, surgeon, electrophysiologist, or other healthcare professional, the user may be patient 14 in some examples.

Programmer 21 may also allow the user to define how LPD 16 and/or subcutaneous ICD system 30 senses electrical signals (e.g., ECGs), detects arrhythmias such as tachyarrhythmias, delivers therapy, and communicates with other devices of system 10. For example, programmer 21 may be used to change tachyarrhythmia detection parameters. In another example, programmer 21 may be used to manage therapy parameters that define therapies such as anti-tachyarrhythmia shocks and/or ATP. Moreover, programmer 21 may be used to alter communication protocols between LPD 16 and subcutaneous ICD system 30. For example, programmer 21 may instruct LPD 16 and/or subcutaneous ICD system 30 to switch between one-way and two-way communication and/or change which of LPD 16 and/or subcutaneous ICD system 30 are tasked with initial detection of arrhythmias.

Programmer 21 may communicate with LPD 16 and/or subcutaneous ICD system 30 via wireless communication using any techniques known in the art. Examples of communication techniques may include, for example, proprietary and non-proprietary radiofrequency (RF) telemetry, but other techniques are also contemplated. In some examples, programmer 21 may include a programming head that may be placed proximate to the patient's body near the LPD 16 and/or subcutaneous ICD system 30 implant site in order to improve the quality or security of communication between LPD 16 and/or subcutaneous ICD system 30 and programmer 21.

LPD 16 may be configured to adjust cardiac therapy based on the application of anti-tachyarrhythmia shock therapy by ICD 20. It is important that LPD 16 knows when ICD 20 has delivered tachyarrhythmia shock therapy. In response to the delivery of the shock, the LPD may terminate ATP and activate post-shock pacing.

In some examples, LPD 16 and subcutaneous ICD system 30 may engage in communication to facilitate the appropriate detection of arrhythmias and/or delivery of anti-tachycardia therapy. Anti-tachycardia therapy may include anti-tachyarrhythmia shocks (e.g., cardioversion or defibrillation pulses) and/or anti-tachycardia pacing (ATP). The communication may include one-way communication in which one device is configured to transmit communication messages and the other device is configured to receive those messages. The communication may instead include two-way communication in which each device is configured to transmit and receive communication messages. Although the examples below describe detection of tachyarrhythmias and the delivery of anti-tachyarrhythmia shocks and/or ATP, LPD 16 and subcutaneous ICD system 30 may be configured to communicate with each other and provide alternative electrical stimulation therapies. Two-way communication and coordination of the delivery of patient therapies between LPD 16 and subcutaneous ICD system 30 is described in commonly-assigned U.S. patent application Ser. No. 13/756,085, titled, "SYSTEMS AND METHODS FOR LEADLESS PACING AND SHOCK THERAPY," filed Jan. 31, 2013, the entire content of which is incorporated by reference herein.

In combination with, or as an alternative to, communication between LPD 16 and subcutaneous ICD system 30, LPD 16 may be configured to detect an anti-tachyarrhythmia shock delivered by subcutaneous ICD system 30 or an external defibrillator according to the detection of an electrical signal across two or more electrodes of LPD 16. LPD 16 may be configured to detect an anti-tachyarrhythmia shock based on electrical characteristics of the anti-tachyarrhythmia shock. Even though different defibrillation devices may provide different waveforms, including different pulse durations and amplitudes, defibrillation pulses generally have electrical signal characteristics such that detection of an anti-tachyarrhythmia shock can occur even without prior knowledge as to an anti-tachyarrhythmia shock waveform of an implanted or external defibrillator. In this manner, LPD 16 may coordinate the delivery of cardiac stimulation therapy, including the termination of ATP and the initiation of the delivery of post-shock pacing, with the application of an anti-tachyarrhythmia shock merely through the detection of defibrillation pulses and without the need to communicate with the defibrillation device applying the anti-tachyarrhythmia shock.

In some examples, LPD 16 detects the anti-tachyarrhythmia shock by measuring the voltage across the electrode inputs of the implanted device. LPD 16 may detect one or more signal characteristics of an anti-tachyarrhythmia shock including: detection of the high amplitude level of an anti-tachyarrhythmia shock, detection of a high slew rate of the leading and trailing edges, and detection of a large post-shock polarization change. Detection of more than one signal characteristic may improve sensitivity and/or specificity. For example, LPD 16 may detect a high level of an anti-tachyarrhythmia shock in combination with one or both of the detection of a high slew rate of the leading and trailing edges, and the detection of a large post-shock polarization change.

In one example, LPD 16 may be configured to receive an indication of a detected cardiac arrhythmia eligible for anti-tachyarrhythmia shock therapy. LPD 16 may include a set of electrodes configured to be implanted within or near heart 18 of patient 14. In response to receiving the indication of the tachyarrhythmia, LPD 16 may enable a shock detector of LPD 16 configured to detect delivery of anti-tachyarrhythmia shock therapy. The shock detector may then detect delivery of anti-tachyarrhythmia shock therapy by measuring the voltage across the electrode inputs (e.g., detect that the shock has been delivered). The shock detector may apply one or more of three general techniques for detection of an anti-tachyarrhythmia shock: detection of the high level of an anti-tachyarrhythmia shock, detection of a high slew rate of the leading and trailing edges, and detection of a large post-shock polarization change. Each technique looks for a different electrical signal characteristic. The three techniques may be combined to improve sensitivity and/or specificity. For example, the high level of an anti-tachyarrhythmia shock may be combined with one or both of the detection of a high slew rate of the leading and trailing edges, and the detection of a large post-shock polarization change.

In response to detection of the anti-tachyarrhythmia shock, the LPD 16 may abort and/or temporarily suspend the delivery of ATP and to activate post-shock pacing, such as VVI (Ventricular sensing, Ventricular pacing, Inhibited pacing when activity sensed) post-shock pacing. ATP may remain suspended temporarily following an anti-tachyarrhythmia shock to insure that the relatively higher-rate pacing pulses will not induce another arrhythmia. Additionally, post-shock pacing may be used to insure pacing support if the patient's heart does not begin to beat normally immediately following an anti-tachyarrhythmia shock. The pacing device may deliver post-shock pacing with a higher than normal pulse amplitude and pulse width (relative to typical cardiac pacing) to minimize the risk of loss of capture following an anti-tachyarrhythmia shock. A higher capture threshold may occur as a result of tissue stunning due to elevated current in the myocardial tissue from the anti-tachyarrhythmia shock delivery. A higher threshold may also occur as a result of physiological changes in the tissue resulting from lack of blood flow to the myocardium during ventricular fibrillation (VF). Furthermore, after an anti-tachyarrhythmia shock there can be increased polarization at the lead interface resulting in the need for a higher voltage to overcome the lead polarization.

In one example, LPD 16 may deliver post-shock pacing to heart 18 via at least a subset of the set of electrodes of LPD 16. In some examples, LPD 16 may deliver the post-shock pacing after entering a post-shock pacing mode in response to detecting the shock. In some examples, LPD 16 may use a timer to determine when a predetermined time has elapsed, during which the shock should have been delivered. LPD 16 may begin post-shock pacing after the predetermined period has elapsed and/or stop post-shock pacing.

LPD 16 may receive the indication of the detected cardiac tachyarrhythmia in a variety of ways. For example, LPD 16 may sense, via at least a subset of the set of electrodes, an electrical signal from heart 18. LPD 16 may then detect, from the electrical signal, a cardiac tachyarrhythmia eligible for anti-tachyarrhythmia shock therapy. In this manner, LPD 16 may receive the indication of the detected arrhythmia via direct detection of the arrhythmia at LPD 16. In another example, subcutaneous ICD system 30 may be configured to transmit a communication including the indication to LPD 16. The indication of the detected arrhythmia may thus be received from subcutaneous ICD system 30, for example. LPD 16 may receive a communication from subcutaneous ICD system 30 indicating that a cardiac arrhythmia was detected by subcutaneous ICD system 30. Alternatively, LPD 16 may receive a communication from subcutaneous ICD system 30 indicating that a shock is impending.

Detection of the anti-tachyarrhythmia shock may be used to abort and/or temporarily suspend the delivery of ATP and to activate post-shock pacing, such as VVI post-shock pacing. ATP may be temporarily suspended following an anti-tachyarrhythmia shock to insure that the pacing pulses will not induce another arrhythmia. For example, ATP may be temporarily suspended following an anti-tachyarrhythmia shock until the current arrhythmia has been terminated or until a short period of time has elapsed to prevent interfering with the subcutaneous ICD.

In addition to the delivery of ATP, LPD 16 may be configured to deliver post-shock pacing to heart 18. After delivery of an anti-tachyarrhythmia shock, heart 18 may benefit from pacing to return to a normal sinus rhythm (e.g., if heart 18 has developed bradycardia or asystole) or otherwise recover from receiving the shock. In some examples, LPD 16 and/or subcutaneous ICD system 30 may be configured to detect bradycardia or asystole. In some examples, this post-shock pacing may be automatically delivered in response to the LPD 16 detecting that a shock was delivered. Post-shock pacing may be used to ensure pacing support if the patient's heart does not begin to beat normally immediately following an anti-tachyarrhythmia shock. A higher than normal amplitude and pulse width is commonly used to minimize the risk of loss of capture following an anti-tachyarrhythmia shock. A higher capture threshold may occur as a result of tissue stunning due to elevated current in the myocardial tissue from the anti-tachyarrhythmia shock delivery. A higher threshold may also occur as a result of physiological changes in the tissue resulting from lack of blood flow to the myocardium during VF. Furthermore, after an anti-tachyarrhythmia shock there can be increased polarization at the lead interface resulting in the need for a higher voltage to overcome the lead polarization.

In some examples, LPD 16 may enable the shock detector when ATP is delivered to heart 18, in anticipation of a shock. In some examples, LPD 16 may enable the shock detector in response to detecting a fast rate, such as a tachyarrhythmia (e.g., when communication between LPD 16 and subcutaneous ICD system 30 is not present or is unreliable). The tachyarrhythmia may be detected based on sensed electrical signals and/or mechanical signals from heart 18. In any example, the shock detector may be disabled until an indication of an arrhythmia is terminated or impending shock is received.

LPD 16 may also be configured to disable the shock detector. For example, LPD 16 may be configured to track a period of time following detection of delivery of anti-tachyarrhythmia shock therapy. The period of time may be a predetermined period of time and/or tracked with a timer, for example. LPD 16 may also determine that the period of time exceeds a timeout threshold, and, in response to the determination, disable the shock detector. LPD 16 may disable the shock detector when not needed to conserve battery power, for example.

LPD 16 may also re-start post-shock pacing if additional shocks are detected. For example, LPD 16 may be configured to detect a first shock and begin delivery of the post-shock pacing if needed (e.g., bradycardia or systole has been detected). LPD 16 may subsequently detect the delivery of a second shock, and, in response to the detection of the second shock, re-start delivery of the post-shock pacing if needed. LPD 16 may continue to re-start post-shock pacing as long as additional shocks are delivered. However, LPD 16 may be configured to stop re-starting post-shock pacing after a predetermined number of shocks, or in response to subcutaneous ICD system 30 transmitting a message instructing LPD 16 to stop delivery of post-shock pacing. LPD 16 and/or subcutaneous ICD system 30 may implement an intrinsic beat detector or other algorithm to distinguish between intrinsic beats and potential artifacts caused by pacing and/or shock therapy. LPD 16 may also deliver ATP upon detection of a tachyarrhythmia, and terminate ATP if a defibrillation pulse is detected. LPD 16 may initiate post-shock pacing and/or, upon detection of additional tachyarrhythmia following the shock, resume ATP.

In some examples, LPD 16 may terminate post-shock pacing in response to various indicators. For example, LPD 16 may track a period of time following the start of post-shock pacing. LPD 16 may then determine that the period of time exceeds a timeout threshold. For example, LPD 16 may use a timer to track this period of time. In response to the determination, LPD 16 may terminate delivery of post-shock pacing. In other examples, LPD 16 may terminate post-shock pacing after delivery of a predetermined number of pacing pulses. Alternatively, LPD 16 may terminate post-shock pacing in response to detection of a normal sinus rhythm or receiving a communication from subcutaneous ICD system 30 instructing LPD 16 to terminate post-shock pacing.

Although LPD 16 is generally described as delivering post-shock pacing, in other examples, different implanted devices may provide post-shock pacing. For example, LPD 16 may be configured to deliver ATP, but a different LPD implanted in a different chamber of heart 18 may be configured to detect a shock and deliver the post-shock pacing to heart 18. In other examples, the implanted device delivering post-shock pacing may not be a leadless pacing device. For example, an implantable pacing device, separate from an ICD delivering the anti-tachyarrhythmia shock, may include one or more leads for delivering post-shock pacing therapy to one or more locations of heart 18. As another example, an ICD delivering the anti-tachyarrhythmia shock may deliver post-shock pacing, whereas LPD is configured to provide ATP, and not post-shock pacing.

Figure 2:
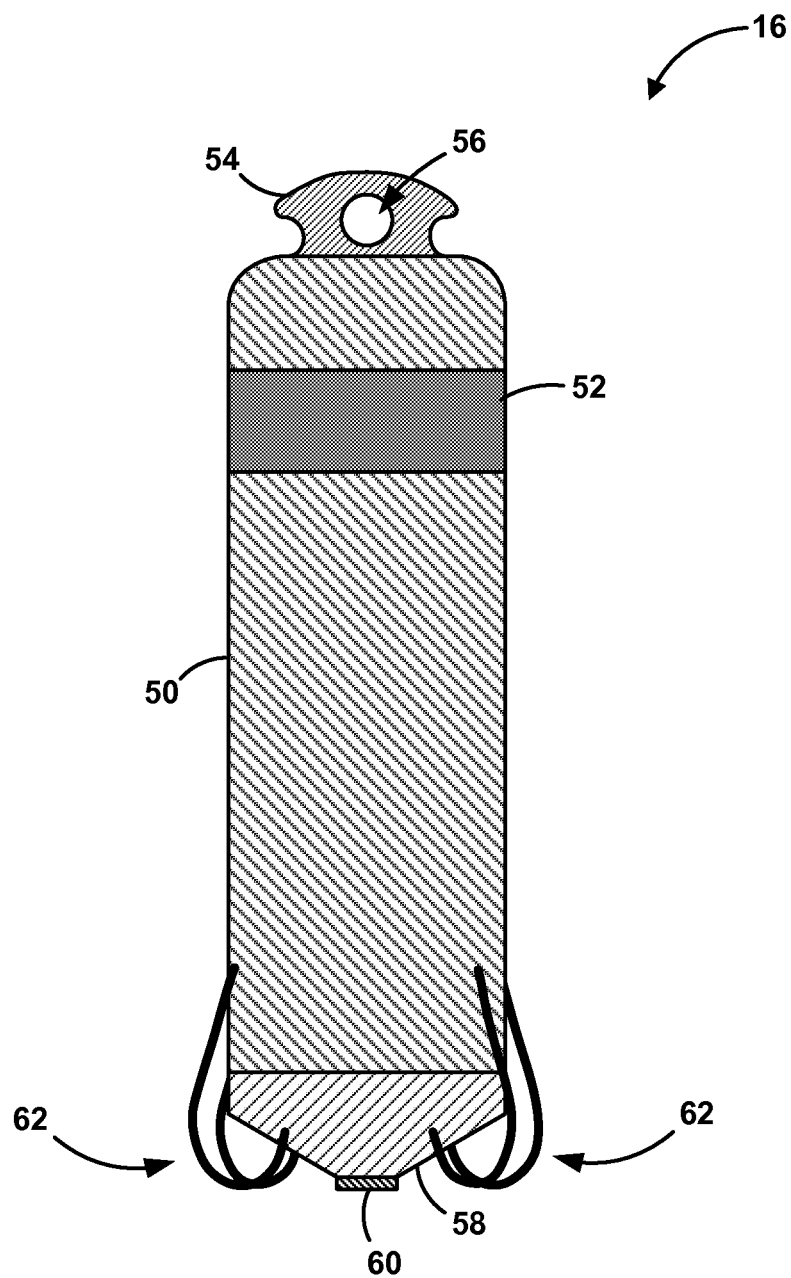
FIG. 2 is a conceptual drawing illustrating the example LPD of FIG. 1.

FIG. 2 is a conceptual drawing illustrating example LPD 16 of FIG. 1 that may include a shock detector and/or utilize the shock detection techniques of this disclosure. As shown in FIG. 2, LPD 16 includes case 50, cap 58, electrode 60, electrode 52, fixation mechanisms 62, flange 54, and opening 56. Together, case 50 and cap 58 may be considered the housing of LPD 16. In this manner, case 50 and cap 58 may enclose and protect the various electrical components within LPD 16. Case 50 may enclose substantially all of the electrical components, and cap 58 may seal case 50 and create the hermetically sealed housing of LPD 16. Although LPD 16 is generally described as including one or more electrodes, LPD 16 may typically include at least two electrodes (e.g., electrodes 52 and 60) to deliver an electrical signal (e.g., therapy such as ATP) and/or provide at least one sensing vector.

Electrodes 52 and 60 are carried on the housing created by case 50 and cap 58. In this manner, electrodes 52 and 60 may be considered leadless electrodes. In the example of FIG. 2, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating. Electrode 60 may be used as a cathode and electrode 52 may be used as an anode, or vice versa, for delivering pacing stimulation therapy such as ATP or post-shock pacing. However, electrodes 52 and 60 may be used in any stimulation configuration. In addition, electrodes 52 and 60 may be used to detect intrinsic electrical signals from cardiac muscle. In other examples, LPD 16 may include three or more electrodes, where each electrode may deliver therapy and/or detect intrinsic signals. ATP delivered by LPD 16, as compared with alternative devices, may be considered to be "painless" to patient 14 or even undetectable by patient 14 since the electrical stimulation occurs very close to or at cardiac muscle and at relatively low energy levels.

Fixation mechanisms 62 may attach LPD 16 to cardiac tissue. Fixation mechanisms 62 may be active fixation tines, screws, clamps, adhesive members, or any other types of attaching a device to tissue. As shown in the example of FIG. 2, fixation mechanisms 62 may be constructed of a memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of LPD 16. For example, a suture or other device may be inserted around flange 54 and/or through opening 56 and attached to tissue. In this manner, flange 54 may provide a secondary attachment structure to tether or retain LPD 16 within heart 18 if fixation mechanisms 62 fail. Flange 54 and/or opening 56 may also be used to extract LPD 16 once the LPD needs to be explanted (or removed) from patient 14 if such action is deemed necessary.

The techniques described herein are generally described with regard to a leadless pacing device such as LPD 16. LPD 16 may be an example of an anti-tachycardia pacing device (ATPD). However, alternative implantable medical devices may be used to perform the same or similar functions as LPD 16 (e.g., delivering ATP to heart 18) and communicate with subcutaneous ICD system 30. For example, an ATPD may include a small housing that carries an electrode, similar to LPD 16, and configured to be implanted within a chamber of heart 18. The ATPD may also include one or more relatively short leads configured to place one or more respective additional electrodes at another location within the same chamber of the heart or a different chamber of the heart. This configuration may be referred to as an Intercardiac Pacing Device (IPD). In this manner, the housing of the ATPD may not carry all of the electrodes used to deliver ATP or perform other functions. In other examples, each electrode of the ATPD may be carried by one or more leads (e.g., the housing of the ATPD may not carry any of the electrodes).

In another example, the ATPD may be configured to be implanted external to heart 18, e.g., near or attached to the epicardium of heart 18. An electrode carried by the housing of the ATPD may be placed in contact with the epicardium and/or one or more electrodes of leads coupled to the ATPD may be placed in contact with the epicardium at locations sufficient to provide therapy such as ATP (e.g., on external surfaces of the left and/or right ventricles). In any example, subcutaneous ICD system 30 may communicate with one or more leadless or leaded devices implanted internal or external to heart 18.

Figure 3:
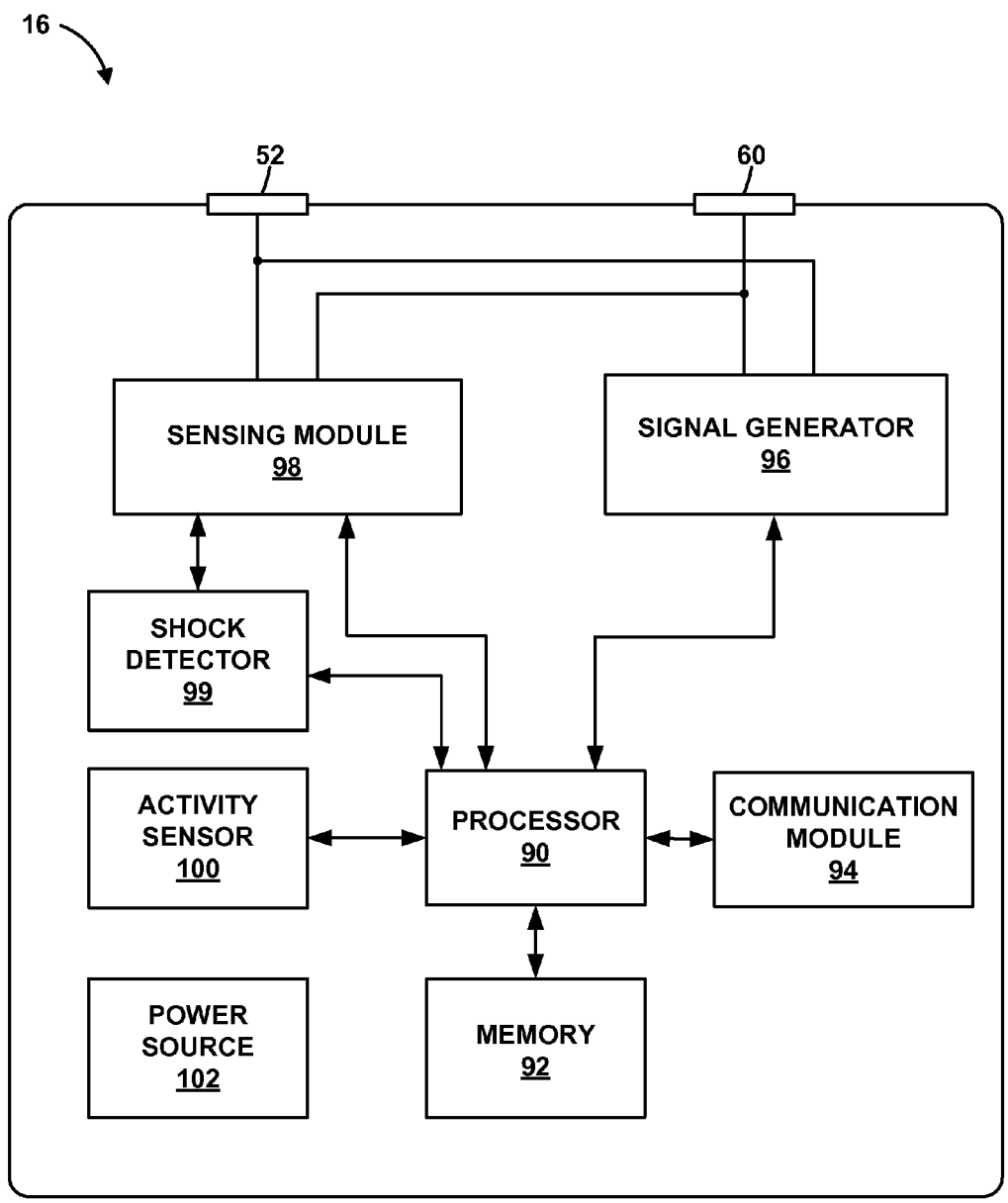
FIG. 3 is a functional block diagram illustrating an example configuration of the LPD of FIG. 1.

FIG. 3 is a functional block diagram illustrating an example configuration of LPD 16 of FIG. 1. In the illustrated example, LPD 16 includes a processor 90, memory 92, signal generator 96, sensing module 98, shock detector 99, activity sensor 100, communication module 94, and power source 102. Memory 92 includes computer-readable instructions that, when executed by processor 90, cause LPD 16 and processor 90 to perform various functions attributed to LPD 16 and processor 90 herein (e.g., detecting arrhythmias, communicating with subcutaneous ICD system 30, and delivering anti-tachycardia pacing and post-shock pacing as well as conventional brady pacing therapy). Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 90 may include any one or more of a microprocessor, a controller, a digital signal processor (DSP), an application specific integrated circuit (ASIC), a field-programmable gate array (FPGA), or equivalent discrete or analog logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof.

Processor 90 controls signal generator 96 to deliver stimulation therapy to heart 18 according to therapy parameters, which may be stored in memory 92. For example, processor 90 may control signal generator 96 to deliver electrical pulses with the amplitudes, pulse widths, frequency, or electrode polarities specified by the therapy parameters. In this manner, signal generator 96 may deliver pacing pulses (e.g., ATP pulses or post-shock pacing therapy, or conventional bradycardia pacing pulses) to heart 18 via electrodes 52 and 60. Although LPD 16 may only include two electrodes, e.g., electrodes 52 and 60, LPD 16 may utilize three or more electrodes in other examples. LPD 16 may use any combination of electrodes to deliver therapy and/or detect electrical signals from patient 14.

Signal generator 96 is electrically coupled to electrodes 52 and 60 carried on the housing of LPD 16. In the illustrated example, signal generator 96 is configured to generate and deliver electrical stimulation therapy to heart 18. For example, signal generator 96 may deliver the electrical stimulation therapy to a portion of cardiac muscle within heart 18 via electrodes 52 and 60. In some examples, signal generator 96 may deliver pacing stimulation, e.g., ATP therapy or post-shock pacing, in the form of voltage or current electrical pulses. In other examples, signal generator 96 may deliver one or more of these types of stimulation in the form of other signals, such as sine waves, square waves, or other substantially continuous time signals. Although LPD 16 is generally described as delivering pacing pulses, LPD 16 may deliver cardioversion or defibrillation pulses in other examples.

ATP may be delivered to patient 14 as defined by a set of parameters. These parameters may include pulse intervals, pulse width, current and/or voltage amplitudes, and durations for each pacing mode. For example, the pulse interval may be based on a fraction of the detected ventricular tachycardia (VT) cycle length and be between approximately 150 milliseconds and 500 milliseconds (e.g., between approximately 2.0 hertz and 7.0 hertz), and the pulse width may be between approximately 0.5 milliseconds and 2.0 milliseconds. The amplitude of each pacing pulse may be between approximately 2.0 volts and 10.0 volts. In some examples, the pulse amplitude may be approximately 6.0 V and the pulse width may be approximately 1.5 milliseconds; another example may include pulse amplitudes of approximately 5.0 V and pulse widths of approximately 1.0 milliseconds. Each train of pulses during ATP may last for a duration of between approximately 0.5 seconds to approximately 15 seconds or be defined as a specific number of pulses. Each pulse, or burst of pulses, may include a ramp up in amplitude or in pulse rate. In addition, trains of pulses in successive ATP periods may be delivered at increasing pulse rate in an attempt to capture the heart and terminate the tachycardia. Example ATP parameters and other criteria involving the delivery of ATP are described in U.S. Pat. No. 6,892,094 to Ousdigian et al., entitled, "COMBINED ANTI-TACHYCARDIA PACING (ATP) AND HIGH VOLTAGE THERAPY FOR TREATING VENTRICULAR ARRHYTHMIAS," and issued on May 10, 2005, the entire content of which is incorporated herein by reference.

Parameters that define post-shock pacing may also vary. In one example, monophasic post-shock pacing therapy may have a pulse width of approximately 1 milliseconds at each phase and a pulse amplitude of approximately 5 volts. The pacing rate may be set to 30-60 beats per minute (0.5-1 hertz). The duration of each post-shock pacing session may be between 10 seconds and 60 seconds, or even longer in other examples. In other examples, pulse widths, pulse amplitudes, and/or durations of post-shock pacing may be greater or lower.

Signal generator 96 may also include circuitry for measuring the capture threshold of electrodes 52 and 60. The capture threshold may indicate the voltage and pulse width necessary to induce depolarization of the surrounding cardiac muscle. For example, signal generator 96 may measure the voltage of pacing signals needed to induce ventricular contractions. In examples in which LPD 16 includes more than two electrodes, signal generator 96 may include a switch module and processor 90 may use the switch module to select, e.g., via a data/address bus, which of the available electrodes are used to deliver pacing pulses. The switch module may include a switch array, switch matrix, multiplexer, or any other type of switching device suitable to selectively couple stimulation energy to selected electrodes. In the instance that the capture threshold exceeds useable limits, processor 90 may withhold delivery of ATP or post-shock pacing. In addition, processor 90 may transmit communication to subcutaneous ICD system 30 if pacing cannot be delivered.

Electrical sensing module 98 monitors signals from electrodes 52 and 60 in order to monitor electrical activity of heart 18, impedance, or other electrical phenomenon. Sensing may be done to determine heart rates or heart rate variability, or to detect arrhythmias (e.g., tachyarrhythmias or bradycardia) or other electrical signals. Sensing module 98 may also include a switch module to select which of the available electrodes (or electrode polarity) are used to sense the heart activity, depending upon which electrode combination, or electrode vector, is used in the current sensing configuration. In examples with several electrodes, processor 90 may select the electrodes that function as sense electrodes, i.e., select the sensing configuration, via the switch module within sensing module 98. Sensing module 98 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 90, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 90 may control the functionality of sensing module 98 by providing signals via a data/address bus.

Processor 90 may include a timing and control module, which may be embodied as hardware, firmware, software, or any combination thereof. The timing and control module may comprise a dedicated hardware circuit, such as an ASIC, separate from other processor 90 components, such as a microprocessor, or a software module executed by a component of processor 90, which may be a microprocessor or ASIC. The timing and control module may implement programmable counters. If LPD 16 is configured to generate and deliver pacing pulses to heart 18, such counters may control the basic time intervals associated with DDD, VVI, DVI, VDD, AAI, DDI, DDDR, VVIR, DVIR, VDDR, AAIR, DDIR and other modes of pacing. Example LPDs that may deliver pacing using such modes are described in U.S. patent application Ser. No. 13/665,492 to Bonner et al., entitled, "LEADLESS PACEMAKER SYSTEM," and filed on Oct. 31, 2012, or in U.S. patent application Ser. No. 13/665,601 to Bonner et al., entitled, "LEADLESS PACEMAKER SYSTEM," and filed on Oct. 31, 2012. U.S. patent application Ser. No. 13/665,492 to Bonner et al. and U.S. patent Ser. No. 13/665,601 to Bonner et al. are both incorporated herein by reference in their entireties.

Intervals defined by the timing and control module within processor 90 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 98 for a time interval during and after delivery of electrical stimulation to heart 18. The durations of these intervals may be determined by processor 90 in response to stored data in memory 92. The timing and control module of processor 90 may also determine the amplitude of the cardiac pacing pulses.

Interval counters implemented by the timing and control module of processor 90 may be reset upon sensing of R-waves and P-waves with detection channels of sensing module 98. In examples in which LPD 16 provides pacing, signal generator 96 may include pacer output circuits that are coupled to electrodes 52 and 60, for example, appropriate for delivery of a bipolar or unipolar pacing pulse to one of the chambers of heart 18. In such examples, processor 90 may reset the interval counters upon the generation of pacing pulses by signal generator 96, and thereby control the basic timing of cardiac pacing functions, including ATP or post-shock pacing.

The value of the count present in the interval counters when reset by sensed R-waves and P-waves may be used by processor 90 to measure the durations of R-R intervals, P-P intervals, P-R intervals and R-P intervals, which are measurements that may be stored in memory 92. Processor 90 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 92 may be configured as a plurality of recirculating buffers, capable of holding series of measured intervals, which may be analyzed by processor 90 in response to the occurrence of a pace or sense interrupt to determine whether the patient's heart 18 is presently exhibiting atrial or ventricular tachyarrhythmia.

In some examples, an arrhythmia detection method may include any suitable tachyarrhythmia detection algorithms. In one example, processor 90 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processor 90 in other examples.

In some examples, processor 90 may determine that tachyarrhythmia has occurred by identification of shortened R-R (or P-P) interval lengths. Generally, processor 90 detects tachycardia when the interval length falls below 220 milliseconds and fibrillation when the interval length falls below 180 milliseconds. In other examples, processor 70 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 92. This interval length may need to be detected for a certain number of consecutive cycles, for a certain percentage of cycles within a running window, or a running average for a certain number of cardiac cycles, as examples. In other examples, additional physiological parameters may be used to detect an arrhythmia. For example, processor 90 may analyze one or more morphology measurements, impedances, or any other physiological measurements to determine that patient 14 is experiencing a tachyarrhythmia.

In the event that an ATP regimen is desired, timing intervals for controlling the generation of ATP therapies by signal generator 96 may be loaded by processor 90 into the timing and control module to control the operation of the escape interval counters therein and to define refractory periods during which detection of R-waves and P-waves is ineffective to restart the escape interval counters for the ATP. An ATP regimen may be desired if processor 90 detects an atrial or ventricular tachyarrhythmia based on signals from sensing module 98, and/or receives a command from another device or system, such as subcutaneous ICD system 30, as examples.

In addition to detecting and identifying specific types of cardiac rhythms, sensing module 98 may also sample the detected intrinsic signals to generate an electrogram or other time-based indication of cardiac events. Processor 90 may also be able to coordinate the delivery of pacing pulses from different LPDs implanted in different chambers of heart 18, such as an LPD implanted in atrium and/or an LPD implanted in left ventricle. For example, processor 90 may identify delivered pulses from other LPDs via sensing module 98 and update pulse timing to accomplish a selected pacing regimen. This detection may be on a pulse-to-pulse or beat-to-beat basis, or on a less frequent basis to make slight modifications to pulse rate over time. In other examples, LPDs may communicate with each other via communication module 94 and/or instructions over a carrier wave (such as a stimulation waveform). In this manner, ATP or post-shock pacing may be coordinated from multiple LPDs.

Shock detector 99 may be used to detect anti-tachyarrhythmia shocks delivered by subcutaneous ICD system 30 or another device. For example, processor 90 may enable shock detector 99 in response to detecting a tachyarrhythmia or receiving a communication indicating that an arrhythmia has been detected or a shock is imminent. Processor 90 may also disable shock detector 99 after a predetermined time period has elapsed or when a shock is otherwise not (or no longer) anticipated. When shock detector 99 is enabled, shock detector 99 may identify when an electrical signal received by sensing module 98 is representative of a cardioversion or defibrillation pulse.

In response to detecting a shock via shock detector 99, processor 90 may begin post-shock pacing when such functionality has been enabled for therapy. Processor 90 may also re-start post-shock pacing in response to detecting additional shocks via shock detector 99. In some examples, processor 90 may terminate ATP upon detection of a shock.

Shock detector 99 may detect an anti-tachyarrhythmia shock, e.g., a defibrillation or cardioversion pulse, delivered by subcutaneous ICD system 30 or an external defibrillator based on the detection of an electrical signal across two or more electrodes. In order to detect the anti-tachyarrhythmia shock, shock detector 99 may detect one or more signal characteristics of an anti-tachyarrhythmia shock including: detection of the high amplitude level of an anti-tachyarrhythmia shock, detection of a high slew rate of the leading and trailing edges, and detection of a large post-shock polarization change. Detection of more than one signal characteristic may improve sensitivity and/or specificity of the shock anti-tachyarrhythmia shock detection. For example, shock detector 99 may detect a high level of an anti-tachyarrhythmia shock in combination with one or both of the detection of a high slew rate of the leading and trailing edges and/or the detection of a large post-shock polarization change.

Memory 92 may be configured to store a variety of operational parameters, therapy parameters, sensed and detected data, and any other information related to the therapy and treatment of patient 14. In the example of FIG. 3, memory 92 may store sensed ECGs, detected arrhythmias, communications from subcutaneous ICD system 30, and therapy parameters that define ATP and/or post-shock pacing regimens. In other examples, memory 92 may act as a temporary buffer for storing data until it can be uploaded to subcutaneous ICD system 30, another implanted device, or programmer 21.

Activity sensor 100 may be contained within the housing of LPD 16 and include one or more accelerometers or other devices capable of detecting motion and/or position of LPD 16. For example, activity sensor 100 may include a 3-axis accelerometer that is configured to detect accelerations in any direction in space. Specifically, the 3-axis accelerator may be used to detect LPD 16 motion that may be indicative of cardiac events and/or noise. For example, processor 16 may monitor the accelerations from activity sensor 100 to confirm or detect arrhythmias. Since LPD 16 may move with a chamber wall of heart 18, the detected changes in acceleration may also be indicative of contractions. Therefore, LPD 16 may be configured to identify heart rates and confirm arrhythmias, such as a tachycardia, sensed via sensing module 98.

Communication module 94 includes any suitable hardware, firmware, software or any combination thereof for communicating with another device, such as programmer 21 or subcutaneous ICD system 30 (FIG. 1). Under the control of processor 90, communication module 94 may receive downlink telemetry from and send uplink telemetry to programmer 21 with the aid of an antenna, which may be internal and/or external. Processor 90 may provide the data to be uplinked to programmer 21 and the control signals for the telemetry circuit within communication module 94, e.g., via an address/data bus. In some examples, communication module 94 may provide received data to processor 90 via a multiplexer.

In some examples, LPD 16 may signal programmer 21 to further communicate with and pass the alert through a network such as the Medtronic CareLink® Network developed by Medtronic, Inc., of Minneapolis, Minn., or some other network linking patient 14 to a clinician. LPD 16 may spontaneously transmit information to the network or in response to an interrogation request from a user.

Power source 102 may be any type of device that is configured to hold a charge to operate the circuitry of LPD 16. Power source 102 may be provided as a rechargeable or non-rechargeable battery. In other example, power source 102 may incorporate an energy scavenging system that stores electrical energy from movement of LPD 16 within patient 14.

Figure 4:
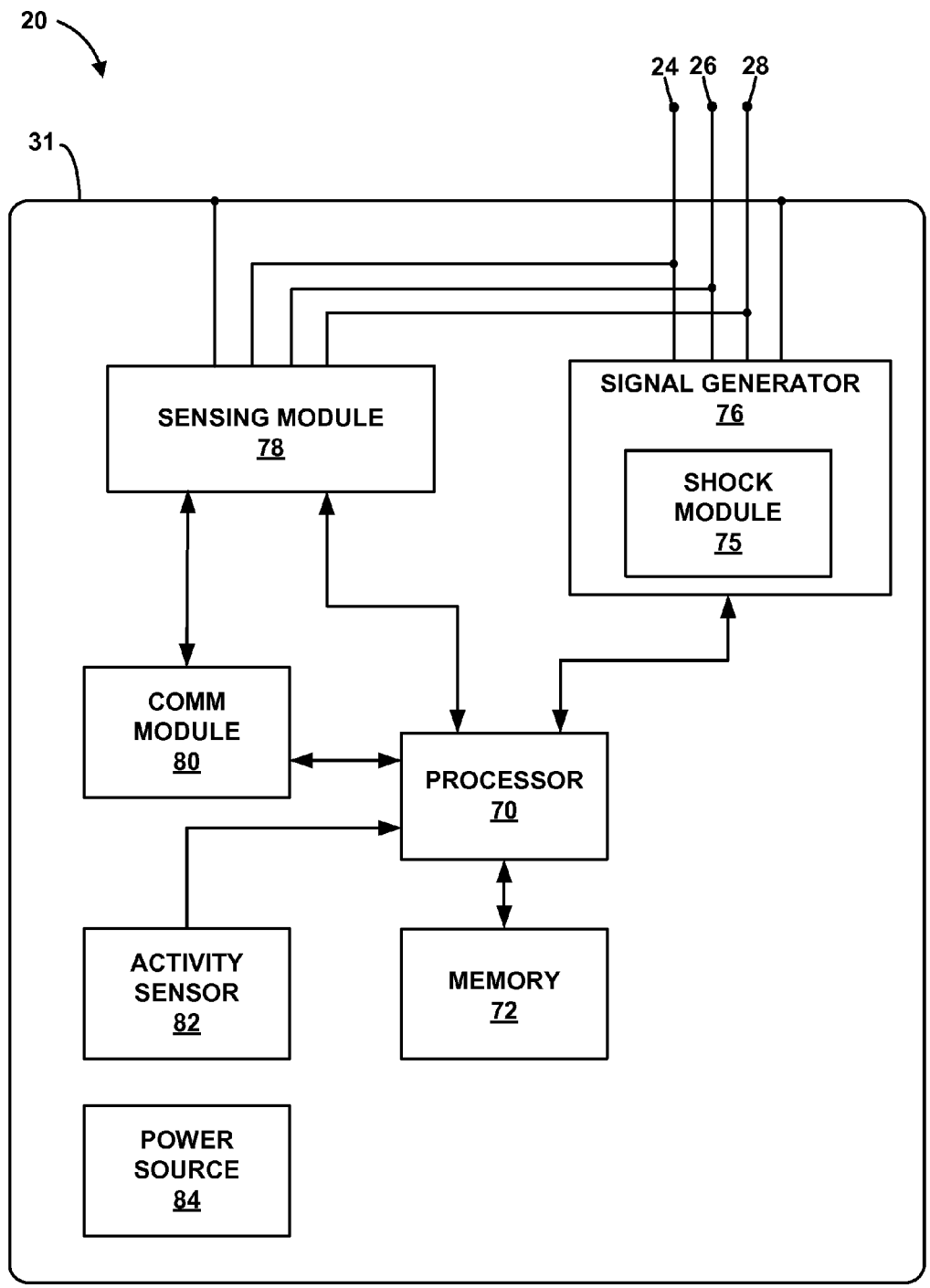
FIG. 4 is a functional block diagram illustrating an example configuration of the subcutaneous ICD of FIG. 1.

FIG. 4 is a functional block diagram illustrating an example configuration of subcutaneous ICD system 30 of FIG. 1. In the illustrated example, subcutaneous ICD system 30 includes a processor 70, memory 72, shock module 75, signal generator 76, sensing module 78, communication module 80, activity sensor 82, and power source 84. Memory 72 includes computer-readable instructions that, when executed by processor 70, cause subcutaneous ICD system 30 and processor 70 to perform various functions attributed to subcutaneous ICD system 30 and processor 70 herein (e.g., detection of tachyarrhythmias, communication with LPD 16, and/or delivery of anti-tachyarrhythmia shock therapy). Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Processor 70 controls signal generator 76 to deliver stimulation therapy to heart 18 according to therapy parameters, which may be stored in memory 72. For example, processor 70 may control signal generator 76 to deliver electrical pulses (e.g., shock pulses) with the amplitudes, pulse widths, frequency, or electrode polarities specified by the therapy parameters. In this manner, signal generator 76 may deliver electrical pulses to heart 18 via electrodes 24 and the conductive housing electrode 31 of ICD 20. In addition, via any combination of electrodes, 24, 26, 28 and/or housing 31 may be connected to sensing module 78. In further examples, signal generator 76 may deliver electrical pulses to heart 18 via any combination of electrodes, 24, 26, 28 and/or housing 31, although electrodes 26 and 28, may more frequently be used for sensing. Subcutaneous ICD system 30 may use any combination of electrodes to deliver anti-tachycardia therapy and/or detect electrical signals from patient 14. However, in general, coil electrode 24 and housing 31 may be used to deliver an anti-tachyarrhythmia shock.

Signal generator 76 may also include shock module 75. Shock module 75 may include circuitry and/or capacitors required to deliver an anti-tachyarrhythmia shock. For example, signal generator 76 may charge shock module 75 to prepare for delivering a shock. Shock module 75 may then discharge to enable signal generator 76 to deliver the shock to patient 14 via one or more electrodes. In other examples, shock module 75 may be located within subcutaneous ICD system 30 but outside of signal generator 76.

Signal generator 76 is electrically coupled to electrodes 24, 26, and 28. In the illustrated example, signal generator 76 is configured to generate and deliver electrical anti-tachyarrhythmia shock therapy to heart 18. For example, signal generator 76 may, using shock module 75, deliver shocks to heart 18 via a subset of electrodes 24, 26, and 28. In some examples, signal generator 76 may deliver pacing stimulation (e.g., post-shock pacing), and cardioversion or defibrillation pulses in the form of voltage or current electrical pulses. In other examples, signal generator 76 may deliver one or more of these types of stimulation or shocks in voltage or current in the form of other signals, such as sine waves, square waves, or other substantially continuous time signals.

Signal generator 76 may include a switch module and processor 70 may use the switch module to select, e.g., via a data/address bus, which of the available electrodes are used to deliver shock and/or pacing pulses. The switch module may include a switch array, switch matrix, multiplexer, or any other type of switching device suitable to selectively couple stimulation energy to selected electrodes.

Electrical sensing module 78 may be configured to monitor signals from at least two of the electrodes 24, 26, 28 and housing 31 in order to monitor electrical activity of heart 18, impedance, or other electrical phenomenon. Sensing may be done to determine heart rates or heart rate variability, or to detect arrhythmias (e.g., tachyarrhythmia) or other electrical signals. Sensing module 78 may also include a switch module to select which of the available electrodes are used to sense the heart activity, depending upon which electrode combination, or electrode vector, is used in the current sensing configuration. In examples with several electrodes, processor 70 may select the electrodes that function as sense electrodes, i.e., select the sensing configuration, via the switch module within sensing module 78. Sensing module 78 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 70, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 70 may control the functionality of sensing module 78 by providing signals via a data/address bus.

Processor 70 may include a timing and control module, which may be embodied as hardware, firmware, software, or any combination thereof. The timing and control module may comprise a dedicated hardware circuit, such as an ASIC, separate from other processor 70 components, such as a microprocessor, or a software module executed by a component of processor 70, which may be a microprocessor or ASIC. The timing and control module may implement programmable counters. If subcutaneous ICD system 30 is configured to generate and deliver pacing pulses to heart 18, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 70 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 78 for a time interval during and after delivery of electrical stimulation to heart 18. The durations of these intervals may be determined by processor 70 in response to stored data in memory 72. The timing and control module of processor 70 may also determine the amplitude of the cardiac pacing pulses.

Interval counters implemented by the timing and control module of processor 70 may be reset upon sensing of R-waves and P-waves with detection channels of sensing module 78. The value of the count present in the interval counters when reset by sensed R-waves and P-waves may be used by processor 70 to measure the durations of R-R intervals, P-P intervals, P-R intervals and R-P intervals, which are measurements that may be stored in memory 72. Processor 70 may use the count in the interval counters to detect a tachyarrhythmia event, such as AF, AT, VF, or VT. These intervals may also be used to detect the overall heart rate, ventricular contraction rate, and heart rate variability. A portion of memory 72 may be configured as a plurality of recirculating buffers, capable of holding series of measured intervals, which may be analyzed by processor 70 in response to the occurrence of a pace or sense interrupt to determine whether the patient's heart 18 is presently exhibiting atrial or ventricular tachyarrhythmia.

In some examples, an arrhythmia detection method may include any suitable tachyarrhythmia detection algorithms. In one example, processor 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processor 70 in other examples.

In some examples, processor 70 may determine that tachyarrhythmia has occurred by identification of shortened R-R (or P-P) interval lengths. Generally, processor 70 detects tachycardia when the interval length falls below 220 milliseconds and fibrillation when the interval length falls below 180 milliseconds. In other examples, processor 70 may detect ventricular tachycardia when the interval length falls between 330 milliseconds and ventricular fibrillation when the interval length falls between 240 milliseconds. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In the event that processor 70 detects an atrial or ventricular tachyarrhythmia based on signals from sensing module 78, and an anti-tachyarrhythmia pacing regimen is desired, timing intervals for controlling the generation of anti-tachyarrhythmia pacing therapies by signal generator 76 may be loaded by processor 70 into the timing and control module to control the operation of the escape interval counters therein and to define refractory periods during which detection of R-waves and P-waves is ineffective to restart the escape interval counters for the an anti-tachyarrhythmia pacing. In addition to detecting and identifying specific types of cardiac rhythms, sensing module 78 may also sample the detected intrinsic signals to generate an electrogram or other time-based indication of cardiac events.

In some examples, communication module 80 may be used to detect communication signals from LPD 16. Instead, LPD 16 may generate electrical signals via one or more electrodes with amplitudes and/or patterns representative of information to be sent to subcutaneous ICD system 30. The electrical signals may be carried by pacing pulses or separate communication signals configured to be detected by subcutaneous ICD system 30. In this manner, communication module 80 may be configured to monitor signals sensed by sensing module 78 and determine when a communication message is received from LPD 16.

In other examples, subcutaneous ICD system 30 may also transmit communication messages to LPD 16 using electrical signals transmitted from one or more of electrodes 24, 26, 28 and housing 31. In this case, communication module 80 may be coupled to signal generator 76 to control the parameters of generated electrical signals or pulses. Alternatively, processor 70 may detect communications via sensing module 78 and/or generate communications for deliver via signal generator 76. Although communication module 80 may be used to communicate using electrical signals via electrodes 24, 26, 28 and housing 31, communication module 80 may alternatively or in addition use wireless protocols, such as RF telemetry, to communicate with LPD 16 or other medical devices. In some examples, communication module 80 may include this wireless communication functionality.

Communication module 80 includes any suitable hardware, firmware, software or any combination thereof for communicating with another device, such as programmer 21 (FIG. 1). Communication module 80 may transmit generated or received arrhythmia data, therapy parameter values, communications between subcutaneous ICD system 30 and LPD 16, or any other information. For example, communication module 80 may transmit information representative of sensed physiological data such as R-R intervals or any other data that may be used by LPD 16 to determine a condition of patient 14. Communication module 80 may also be used to receive updated therapy parameters from programmer 21. Under the control of processor 70, communication module 80 may receive downlink telemetry from and send uplink telemetry to programmer 21 with the aid of an antenna, which may be internal and/or external. Processor 70 may provide the data to be uplinked to programmer 21 and the control signals for the telemetry circuit within communication module 80, e.g., via an address/data bus. In some examples, communication module 80 may provide received data to processor 70 via a multiplexer.

Memory 72 may be configured to store a variety of operational parameters, therapy parameters, sensed and detected data, and any other information related to the monitoring, therapy and treatment of patient 14. Memory 72 may store, for example, thresholds and parameters indicative of tachyarrhythmias and/or therapy parameter values that at least partially define delivered anti-tachyarrhythmia shocks. In some examples, memory 72 may also store communications transmitted to and/or received from LPD 16.

Activity sensor 82 may be contained within the housing of subcutaneous ICD system 30 and include one or more accelerometers or other devices capable of detecting motion and/or position of subcutaneous ICD system 30. For example, activity sensor 82 may include a 3-axis accelerometer that is configured to detect accelerations in any direction in space. Accelerations detected by activity sensor 82 may be used by processor 70 to identify potential noise in signals detected by sensing module 78 and/or confirm the detection of arrhythmias or other patient conditions.

In some examples, subcutaneous ICD system 30 may signal programmer 21 to further communicate with and pass the alert through a network such as the Medtronic CareLink® Network developed by Medtronic, Inc., of Minneapolis, Minn., or some other network linking patient 14 to a clinician. Subcutaneous ICD system 30 may spontaneously transmit the diagnostic information to the network or in response to an interrogation request from a user.

Power source 84 may be any type of device that is configured to hold a charge to operate the circuitry of subcutaneous ICD system 30. Power source 84 may be provided as a rechargeable or non-rechargeable battery. In other examples, power source 84 may also incorporate an energy scavenging system that stores electrical energy from movement of subcutaneous ICD system 30 within patient 14.

Figure 5A:
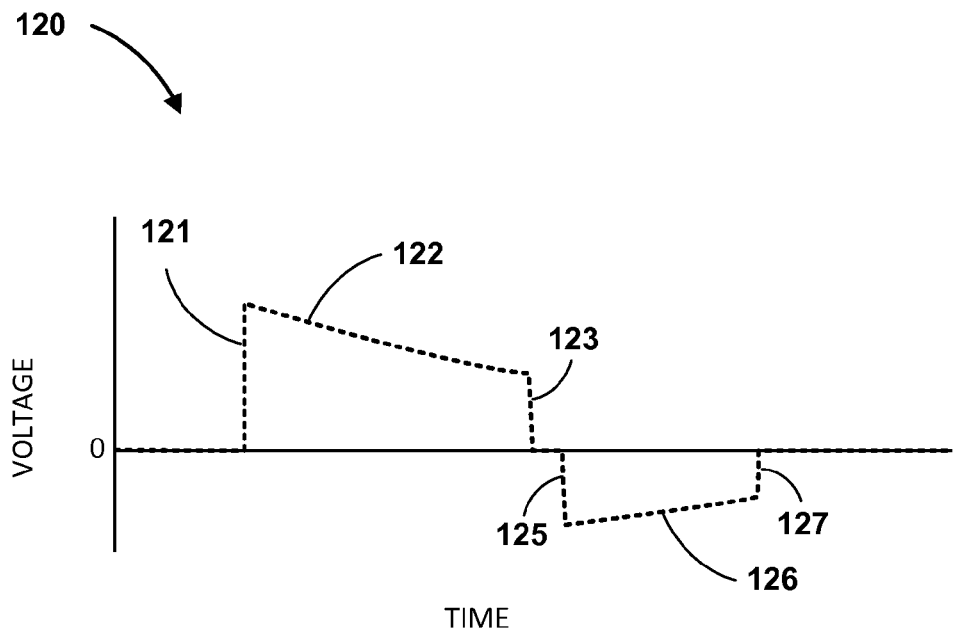
FIG. 5A and FIG. 5B illustrate defibrillation pulse examples from two different defibrillators. The examples may be representative of defibrillation pulses from both ICDs and AEDs.
Figure 5B:
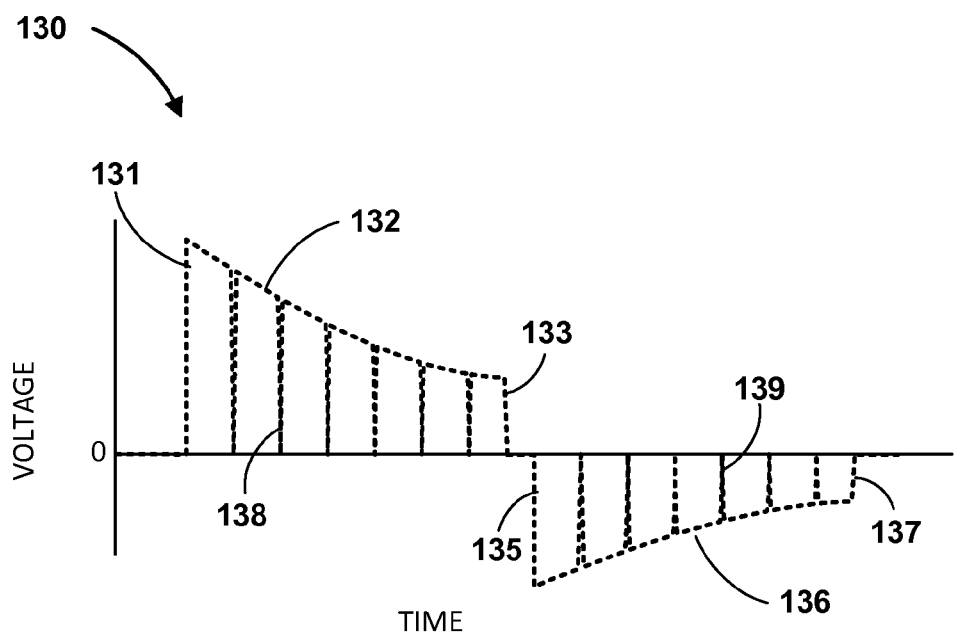

FIG. 5A and FIG. 5B illustrate defibrillation pulse waveforms 120, 130, respectively. Defibrillation pulse waveforms 120, 130 are examples of defibrillation pulse waveforms generated by two different defibrillators. The examples may be representative of defibrillation pulses from both implantable cardiac defibrillators, e.g., ICDs, and automated external defibrillators, e.g., AEDs. Even though defibrillation pulse waveforms 120, 130 are from different defibrillators, they both include common features that may be detected by an implantable cardiac stimulator, such as LPD 16.

Defibrillation pulses can be monophasic or biphasic. The energy of the pulse is typically stored onto a capacitor, connected to the electrodes for a few milliseconds, and then disconnected allowing the voltage on the electrodes to return to 0V. This results in a rapid leading edge, exponential decay due to the tissue load and storage capacitor, and fast falling edge. The amplitude of the second phase of the pulse is typically lower than the first since the storage capacitor has been partially discharged by the first phase of the pulse. The combination of very fast rise/fall time, such as about 1 microsecond, and large amplitude (200V-6000V) and duration (such as a few milliseconds) can be used to identify the signal as an anti-tachyarrhythmia shock.

Defibrillation pulses are typically applied from large area electrodes that are separated by a distance of several inches. The voltage level picked up by LPD electrodes, such as electrodes of LPD 16, depends primarily on electrode separation and orientation of the LPD electrodes relative to the ICD or external defibrillator electrodes. In general, an anti-tachyarrhythmia shock seen across the LPD electrodes will vary from zero to five percent of the voltage applied across the subcutaneous ICD electrodes with a typical value of about two percent. In one example, an anti-tachyarrhythmia shock seen across the LPD electrodes equals two percent of the voltage applied across the subcutaneous ICD electrodes. Such an example may provide an amplitude of about 30 volts for a 1.5 to 2 centimeter electrode spacing on the LPD when implanted in the right ventricle apex. As mentioned above, numerous factors affect the amplitude of an anti-tachyarrhythmia shock seen across the LPD electrodes, and the amplitudes may vary accordingly. Analyzing additional pulse characteristics in addition to, or as an alternative to signal amplitude, may provide improve defibrillation pulse detection.

An anti-tachyarrhythmia shock from an ICD or AED, such as those of defibrillation pulse waveforms 120, 130, has extremely fast or steep edges, e.g., with rapidly changing voltage values, on the leading and trailing edges of each of the positive and negative pulse pairs. A typical mono-phasic shock will have 1 fast leading edge, and 1 fast trailing edge. A typical bi-phasic shock will have 4 fast edges (2 fast edges per pulse). As shown in FIG. 5A, biphasic defibrillation pulse waveform 120 includes fast edges 121, 123, 125 and 127. As shown in FIG. 5B, biphasic defibrillation pulse waveform 130 includes fast edges 131, 133, 135, 137 as well as a series of intermediate edges 138, as both the positive and negative pulses are segmented.

A typical defibrillation pulse from an ICD or AED, such as those of defibrillation pulse waveforms 120, 130, also has an extremely large amplitude as compared to other electrical signals that may be detected by an implantable cardiac stimulator, indicated as amplitudes 122, 126, 132, 136 on defibrillation pulse waveforms 120, 130. As discussed with respect to FIGS. 6A and 6B, below, the fast edges and the high amplitude typical of a defibrillation waveform may be used either separately or together to determine when an anti-tachyarrhythmia shock has occurred.

Figure 6A:
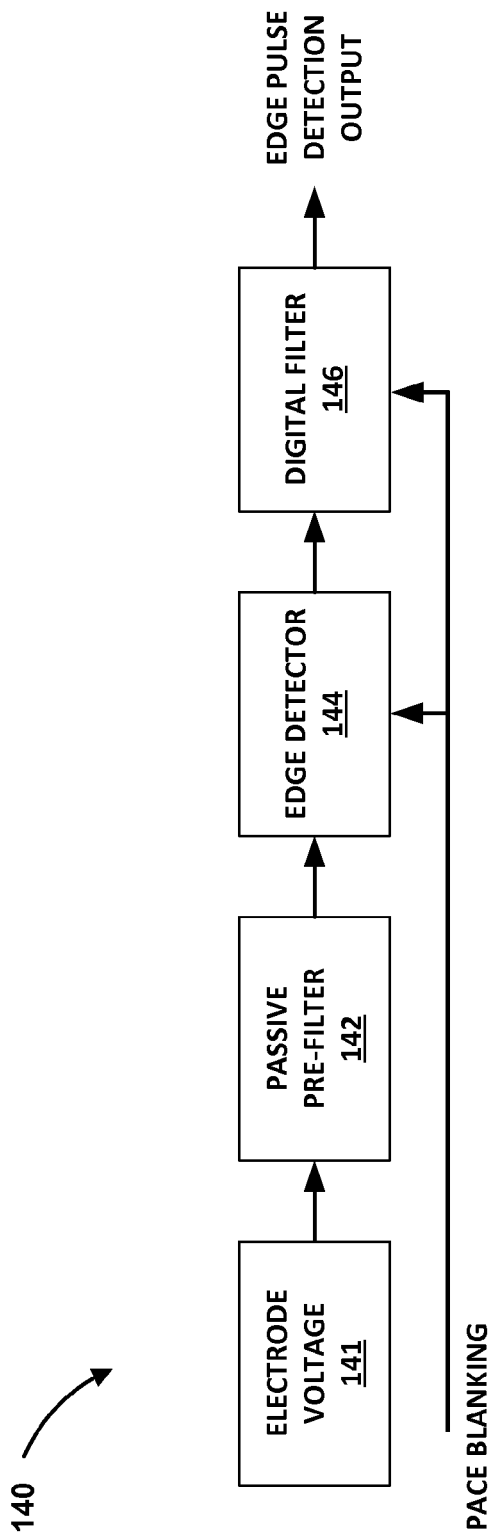
Figure 6B:
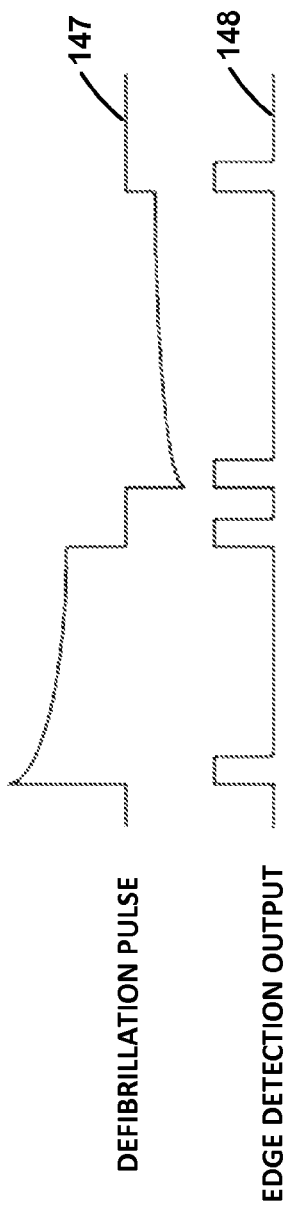
FIG. 6B illustrates an anti-tachyarrhythmia shock signal edge detector output waveform during an anti-tachyarrhythmia shock.

FIG. 6A illustrates anti-tachyarrhythmia shock signal edge detector 140, whereas FIG. 6B illustrates an anti-tachyarrhythmia shock signal edge detector output waveform 148 during defibrillation pulse 147. Anti-tachyarrhythmia shock signal edge detector 140 may be implemented by shock detector 99 of FIG. 3. Anti-tachyarrhythmia shock signal edge detector 140 first receives an input of an electrical voltage across the sensing electrodes, such as electrodes 52, 60 of LPD 16. The sensed voltage passes through pre-filter 142 before being received by edge detector 144. In one example, pre-filter 142 may serve as a high pass filter or differentiator to pass the fast edges through to edge detector 144. Pre-filter 142 may also provide some low pass filtering, e.g., for frequencies greater than 10-100 kilohertz, to reduce the impact of high frequency EMI on edge detector 144 and to provide time for edge detector 144 to see the response. Pre-filter 142 may also may eliminate any DC offsets between electrodes 52 and 60 of LPD 16. In different examples, pre-filter 142 may be a passive or active filter.

Anti-tachyarrhythmia shock signal edge detector 144 detects the edges of high amplitude pulses, as shown in FIG. 6B. For example, edge detector 144 detects a high amplitude voltage change over a time period of not greater than 2 milliseconds, such as over a time a period of about 1 millisecond. For example, a 200-kilohertz high pass filter will lose sensitivity for changes slower than about 1.5 milliseconds, and other high pass filters will sensitivity in a similar manner according to their design and specifications.

If electrical voltage signal 141 is sensed using pacing electrodes, e.g., electrodes 52 and 60 of LPD 16, edge detector 144 will be blanked during pacing. Blanking is used during a pace and discharge sequence to prevent a large amplitude pacing pulse from being detected as a defibrillation pulse. During pace blanking, edge detector 144 may be unable to detect an anti-tachyarrhythmia shock coincident with a pacing pulse. A single edge, as shown in FIG. 6B is sufficient to detect an anti-tachyarrhythmia shock, for this reason, even if a portion of an anti-tachyarrhythmia shock is hidden during pace blanking, anti-tachyarrhythmia shock signal edge detector 144 may still be able to detect an anti-tachyarrhythmia shock. In the example of LPD 16, the sensing electrodes may include tip electrode 60 and ring electrode 52 of LPD 16. If the edges from the anti-tachyarrhythmia shock fall entirely within the pace blanking period, the anti-tachyarrhythmia shock may not be detected. However, if one of the edges falls outside the blanking period the anti-tachyarrhythmia shock will be detected. In addition, as discussed in further detail with respect to FIGS. 10-13, a pacing pulse may include a short sensing period, in which a pacing pulse is divided into two or more windows separated by a period of no electrical stimulation, to limit the impact of blanking caused by the pacing pulse on the sensing capabilities of anti-tachyarrhythmia shock signal edge detector 140 when implemented as part of an implantable cardiac stimulator, such as LPD 16. In such examples, the timing of the stimulation delivered by the implantable cardiac stimulator is selected such that the blanking windows caused by the delivery of the stimulation are short enough that some portion of the anti-tachyarrhythmia shock signal at the implantable cardiac stimulator electrodes will fall outside blanking and be detectable.

Anti-tachyarrhythmia shock signal edge detector 144 detects the edges of high amplitude pulses and passes that information onto digital filter 146 that determines if the edges are due to an anti-tachyarrhythmia shock. An anti-tachyarrhythmia shock that is completely hidden during pace blanking may still be detected by alternative techniques. For example, pace blanking timing is sent to digital filter 146, which may help facilitate detection of an anti-tachyarrhythmia shock based on alternative techniques, such as defibrillation pulse polarization detector 160, as described with respect to FIG. 8.

Figure 7A:
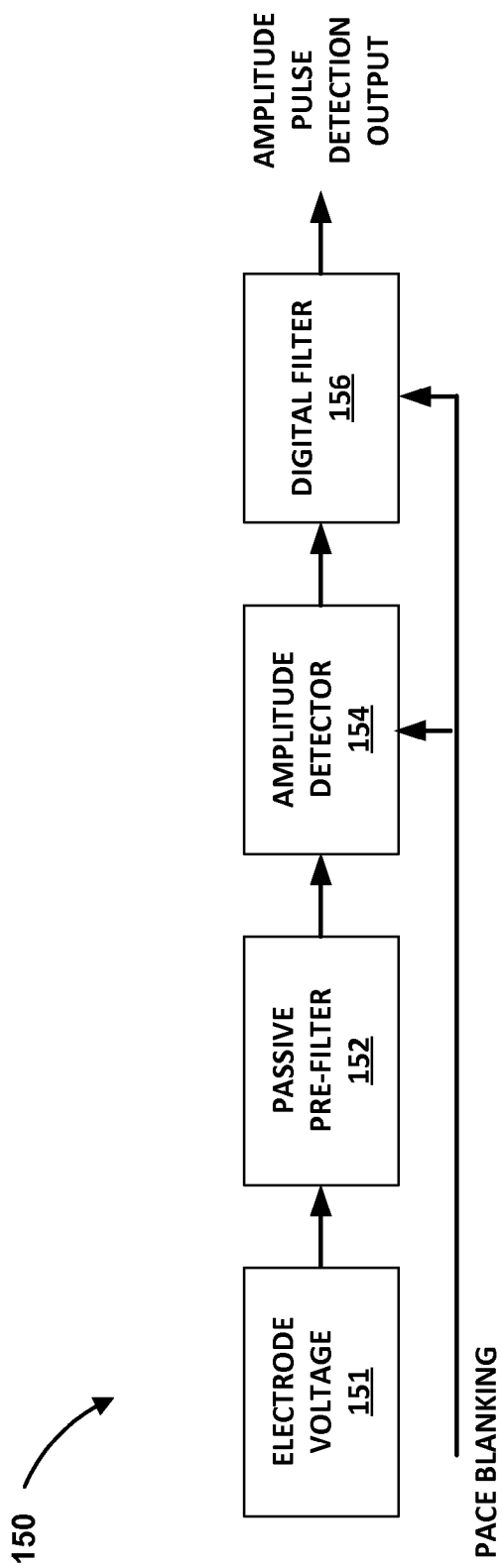
Figure 7B:
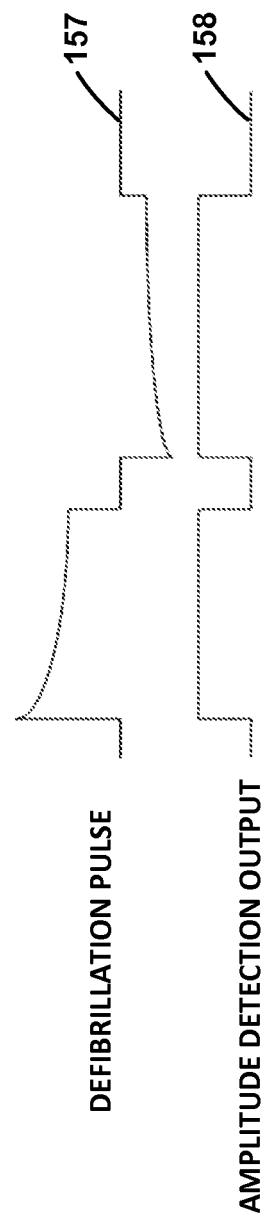
FIG. 7B illustrates an anti-tachyarrhythmia shock amplitude detector output waveform during an anti-tachyarrhythmia shock.

FIG. 7A illustrates signal amplitude detector 150, whereas FIG. 7B illustrates signal amplitude detector output waveform 158 during defibrillation pulse 157. Signal amplitude detector 150 may be implemented by shock detector 99 of FIG. 3. Signal amplitude detector 150 first receives an input of an electrical voltage across the sensing electrodes, such as electrodes 52, 60 of LPD 16. The sensed voltage passes through pre-filter 152 before being received by amplitude detector 154. Pre-filter 152 may be configured to remove signal frequencies from the electrical voltage signal, e.g., frequencies associated with EMI, such as frequencies greater than 1-10 kilohertz. Pre-filter 152 may also eliminate any DC offsets between electrodes, such as tip electrode 60 and ring electrode 52 of LPD 16.

Signal amplitude detector 154 is configured to detect an anti-tachyarrhythmia shock. As shown in FIG. 7B, when signal amplitude detector 154 detects a high amplitude signal across the sensing electrodes, it outputs an indication of the high amplitude signal to digital filter 156.

Digital filter 156 determines if the voltage amplitudes are due to an anti-tachyarrhythmia shock according to the timing of the voltage amplitudes. If electrical voltage signal 151 is being sensed using pacing electrodes, such as tip electrode 60 and ring electrode 52 of LPD 16, amplitude detector 154 will be blanked during pacing according to the pace blanking timing signal sent to digital filter 156. If an anti-tachyarrhythmia shock overlaps the pace pulse blanking window, digital filter 156 will attempt to piece the information together to determine if the voltage amplitude levels were due to a subcutaneous defibrillation pulse. However, if a portion of high voltage amplitude levels of a subcutaneous defibrillation pulse fall outside the blanking period, the anti-tachyarrhythmia shock will be detected. In addition, as discussed in further detail with respect to FIGS. 10-13, a pacing pulse may include a short sensing period, in which a pacing pulse is divided into two or more windows separated by a period of no electrical stimulation, to limit the impact of blanking caused by the pacing pulse on the sensing capabilities of signal amplitude detector 150 when implemented as part of an implantable cardiac stimulator, such as LPD 16.

Figure 8:
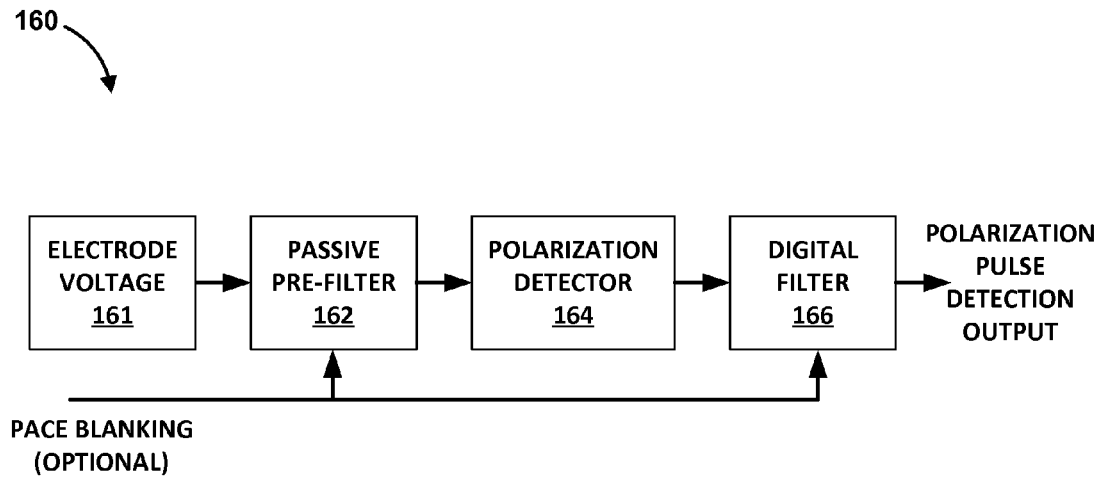
FIG. 8 is a functional block diagram illustrating an example of an anti-tachyarrhythmia shock polarization detector, which may be effective at detecting defibrillation events that occur during pace blanking.

FIG. 8 illustrates defibrillation pulse polarization detector 160, which may be included as part of shock detector 99 of LPD 16. Defibrillation pulse polarization detector may be effective at detecting defibrillation events that occur during pace blanking, even without modification of a standard pacing pulse to include a sensing period. Defibrillation pulse polarization detector 164 is configured to detect a change in the DC polarization level at the sensing electrodes, such as electrodes 52, 60 of LPD 16, due to a defibrillation pulse as reflected in electrode voltage signal 161.

Defibrillation pulse polarization detector 160 first receives an input of an electrical voltage across the sensing electrodes, such as electrodes 52, 60 of LPD 16. The sensed voltage passes through pre-filter 162 before being received by polarization detector 164. Pre-filter 162 may serve as a high pass filter and/or differentiator. If a large voltage is applied across sensing electrodes, such the tip and ring electrodes of LPD 16, the voltage will be clamped by the input protection network of LPD 16 or other implantable pacing device, resulting in a large current flow. This large current may result in a large polarization voltage between the sensing electrodes. As an example, if the open circuit between sensing electrodes is 50 volts as a result of an anti-tachyarrhythmia shock, Zener protection diodes of the device clamp at 10 volts, and the impedance between the electrodes is 500 ohms, there will be a current of 40 volts/500 ohms equals 80 milliamps. A current of 80 milliamps applied for 5 milliseconds duration of an anti-tachyarrhythmia shock results in a total charge of 400 microcoulombs into the sensing electrodes, resulting in electrode voltage 161. If the sensing electrodes capacitance is 400 microfarad, a polarization voltage of about 1 volt will result. This large "DC" polarization voltage will typically remain for a long time, likely much longer than 10 milliseconds, and perhaps seconds following an anti-tachyarrhythmia shock, thereby creating signature of an anti-tachyarrhythmia shock detectable well after the anti-tachyarrhythmia shock. While the electrical configuration of sensing electrodes within an LPD is much more complex than a simple resistor and capacitor, the basic concepts of capacitance and resistance still apply. The particular design of a cardiac stimulator, such as LPD 16, may be tested in a controlled setting to determine the signature polarization voltage of an anti-tachyarrhythmia shock for that particular design of a cardiac stimulator.

Polarization detector 160 may be especially useful at detecting defibrillation pulses that occur during pace blanking. In defibrillation pulse amplitude detector 150 and anti-tachyarrhythmia shock signal edge detector 140, an anti-tachyarrhythmia shock that occurs entirely within pace blanking may be undetected. In contrast, polarization detector 160 may detect a significant change in voltage, e.g., greater than a threshold across sensing electrodes, from before a pace blanking period to after the pace blanking period as an indication of a defibrillation pulse. Typically, after a pace there will be a relatively smaller polarization which decays away over several milliseconds following the pace and discharge sequence. In contrast, polarization resulting from an anti-tachyarrhythmia shock will be much larger and/or longer lasting than polarization resulting from a pace.

Digital filter 166 may be used to analyze the change in voltage from before a pace blanking period to after the pace blanking period to detect the presence of an anti-tachyarrhythmia shock. In addition, as discussed in further detail with respect to FIGS. 10-13, a pacing pulse may include a short sensing period, in which a pacing pulse is divided into two or more windows separated by a period of no electrical stimulation, to improve the sensing capabilities of polarization detector 160 when implemented as part of an implantable cardiac stimulator, such as LPD 16, by limiting the duration of any pace blanking period, thereby further increasing the sensitivity of polarization detector 160.

The detection techniques discussed with respect to FIGS. 6A-8 may be combined in any manner, e.g., any one or more of the detection techniques may be implemented in shock detector 99 of LPD 16. In addition, implementation of the detection techniques discussed with respect to FIGS. 6A-8 may vary from the examples described above. In some examples, multiple detectors may be used to increase sensitivity. In some particular examples, an amplitude detector may be combined with either an edge detector to improve sensitivity just prior to and after blanking or alternatively with a polarization detector to improve sensitivity for shocks occurring during blanking. In addition, a detector, such as any of detectors 140, 150, 160, may be blanked during pacing pulses, either electrically or through digital filtering, to prevent detecting pacing pulses as defibrillation pulses.

Digital filtering, such as that provided by filters 146, 156, 166, may be used to discriminate between electro-surgery, RF ablation, and other electrical signals as compared to an anti-tachyarrhythmia shock. In this manner, such digital filtering provide an additional level of discrimination to prevent high current events such as electro-surgery, RF ablation, EMI, or continuous wave induction from being detected as a HV therapy. Defibrillation waveforms typically have durations of approximately 5 milliseconds per phase, but this may vary depending on the load impedance and manufacturer from a minimum of about 1-2 milliseconds to a maximum of about 15-30 milliseconds per phase. Electro-surgery and RF ablation equipment typically use high frequencies much higher than a defibrillation pulse (100 kilohertz to 1 megahertz). In one example, digital filtering may detect these very high frequencies and block a digital shock detect signal from being generated when the comparators are toggling at frequencies greater than approximately 100 kilohertz.

When an ICD is implanted may be tested to insure it is capable of defibrillating the patient. Testing the ICD may include inducing ventricular fibrillation. Induction waveforms typically use a continuous wave AC current of 0.2 amps with a frequency of approximately 50 hertz and a total duration between 1 and 10 seconds. Digital filtering may detect the induction by detecting that the comparators are toggling at a rate greater than 25 hertz for a time period longer than expected for a defibrillation pulse, such as 100 milliseconds. When a long burst of AC current is detected, a digital filter may generate a signal indicating that a continuous AC signal has been detected and either block the digital shock detect signal from being generated or generate a signal which can be used by the CPU to prevent acting on the falsely detected shock. Detecting continuous wave EMI may also be useful to prevent false detections of shocks in the presence of extreme EMI sources such as welding equipment or high voltage power lines. A digital filter may also include the capability to allow only one shock detection pulse to be generated from each defibrillation pulse regardless of the number of edges or phases detected by preventing pulses from being generated at a rate no faster than approximately once every 100 milliseconds. A digital filter may do this by requiring a time interval of approximately 100 milliseconds without any detections from the comparator before allowing another shock detect to be generated by the digital filter.

In examples in which a shock detector implements two or more of detectors 140, 150, 160, the detectors may implement common functionality as common hardware and/or software. For example, the same hardware used to detect the large amplitude associated with an anti-tachyarrhythmia shock may detect the level change associated with a polarization shift during blanking. As another example, the same hardware used to detect the large amplitude could be used for edge detection if the bandpass filter is shifted. In addition, within an implantable cardiac stimulator, such as LPD 16, a sense amplifier used to detect cardiac signals, including, but not limited to, R-waves and P-waves may also be used to detect defibrillation pulses, although the range of the detected electrical signals associated with defibrillation pulses will generally be different from the ranges of cardiac signals. For example, sensing electrical signals associated with defibrillation pulses may result in sensing electrical signals of a magnitude exceeding about 50 millivolts, whereas sensing cardiac signals may result in sensing electrical signals of a magnitude less than about 50 millivolts.

In one particular example, a typical comparator may have a threshold exceeding about 50 millivolts, such as set to 100 millivolts. In the example of a threshold set to 100 millivolts, an input signal of about 200 millivolts-peak would result in a filtered signal exceeding the 100 millivolts threshold. In some examples, a comparator threshold may be adjustable, such as adjustable with a range of about 50 millivolts to about 200 millivolts, which may be suitable for a device with an electrode spacing, such as tip to ring electrode spacing of about 1.8 centimeters. However, suitable threshold settings or ranges may vary for different electrode configurations and/or spacings. For example, devices with larger or smaller tip to ring spacing may need higher or lower threshold voltage. Generally, the threshold should be set above the maximum expected input level for EMI, intrinsic events, and pacing polarization with sufficient margin to generally avoid detection of a combinations of all of these events while still allowing capture of defibrillation events.

In the particular example of the same hardware being used to detect an amplitude and edge detection (as with detectors 140 and 150), the bandpass filter provided by pre-filter modules 142, 152, 162 may be modified. Such an implementation may include a 1 nanofarad EMI filter capacitor adjacent to the electrodes with an input clamped by Zener-triggered triac of plus or minus 2 volts, a 1 megaohm limit resistor, the resistor may be shared with a cardiac signal sense amplifier, ESD input protect diodes of plus or minus 1 volts, also shared with the cardiac signal sense amplifier. A bandpass filter may include a 5 kilohertz low pass filter shared with the cardiac signal sense amplifier, a 200 hertz high pass filter to suppress DC offset and polarization and a 1 kilohertz low pass filter to suppress EMI. Such defibrillation detection hardware may further include an adjustable threshold of plus or minus 50-300 millivolts, two clocked comparators to detect threshold crossing and further include digital filtering for excessive EMI. These specific references to hardware for detection defibrillation pulses are merely examples and any number of modifications may be made to the digital and analog hardware implementations described.

As discussed previously, detection of an anti-tachyarrhythmia shock may be used to adjust the functionality of a cardiac stimulator, such as LPD 16. For example, following the detection of an anti-tachyarrhythmia shock, the cardiac stimulator may perform one or more actions, including, but not limited to: aborting ATP, initiating post-shock pacing, increasing pacing amplitude and pulse width after the shock to increase likelihood of capture if the anti-tachyarrhythmia shock causes temporary rise in capture threshold due to stunning or polarization on lead interface, resetting the V-V timing so the first pace after a shock occurs at correct V-V time delay, clearing off the pacing AC coupling capacitor so any charge built up on the capacitor or at the lead interface will not impact delivered pacing amplitude, recharging the pacing capacitor to the correct voltage in case the anti-tachyarrhythmia shock affects the voltage by causing switches to turn on, temporarily switching in a lower value resistor, such as a 20 kilo-ohm rather than 5 mega-ohm resistor, to bleed the polarization/charge off the lead interface and/or AC coupling capacitor after a shock, and increasing discharge time and/or blanking times for the sense amplifier to reduce likelihood of over sensing the lead polarization after a pace. In addition, the cardiac stimulator may flag the event of the detection of the anti-tachyarrhythmia shock and store for diagnostic information.

Figure 9A:
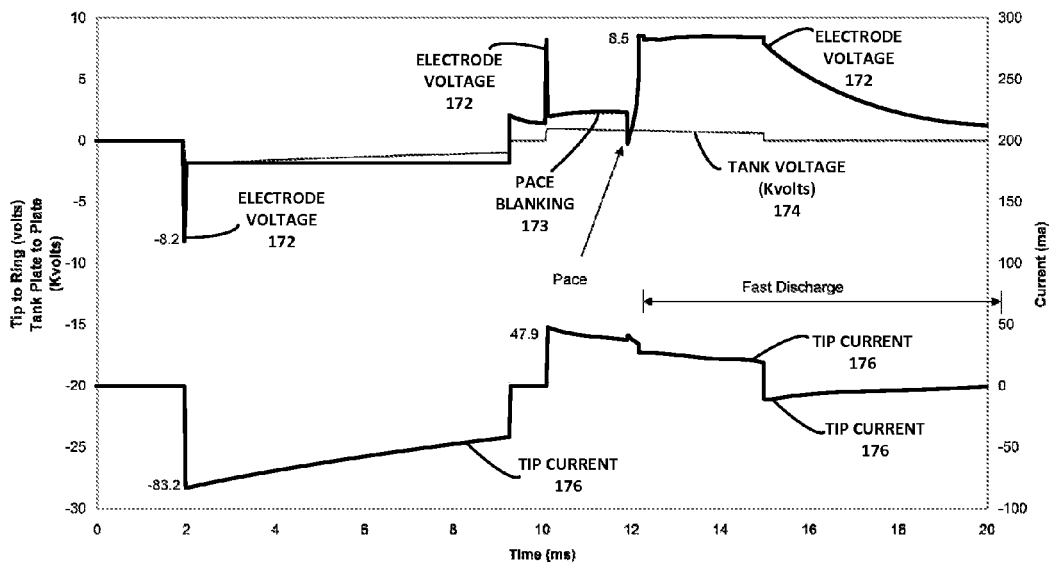
FIGS. 9A-9C illustrate examples of defibrillation pulse polarization resulting from a defibrillation pulse occurring on or shortly after a pacing pulse.
Figure 9B:
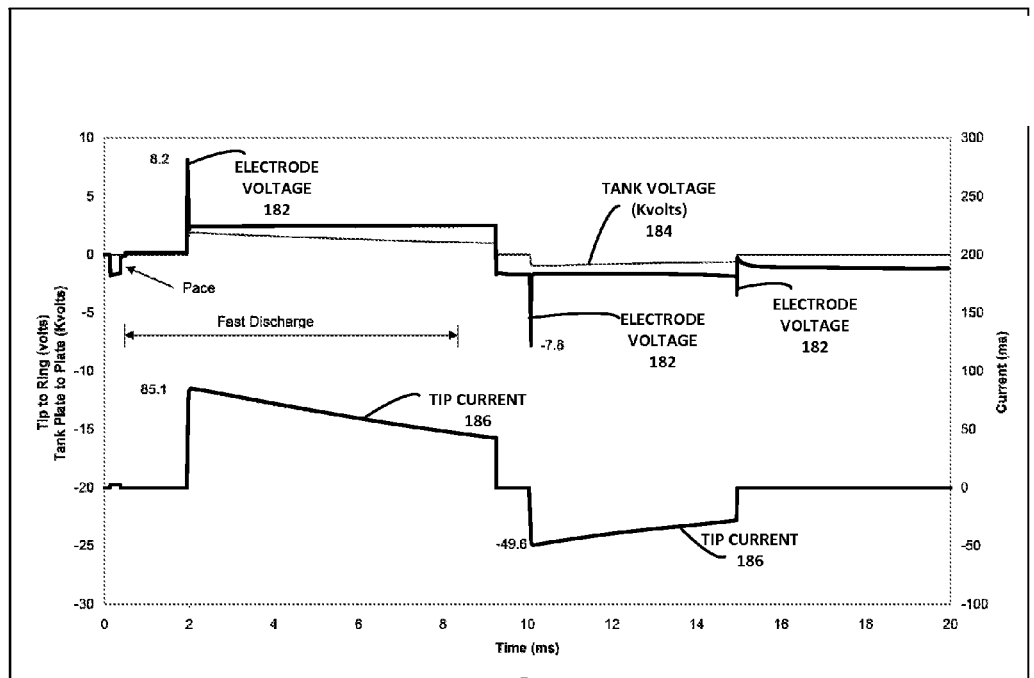
Figure 9C:
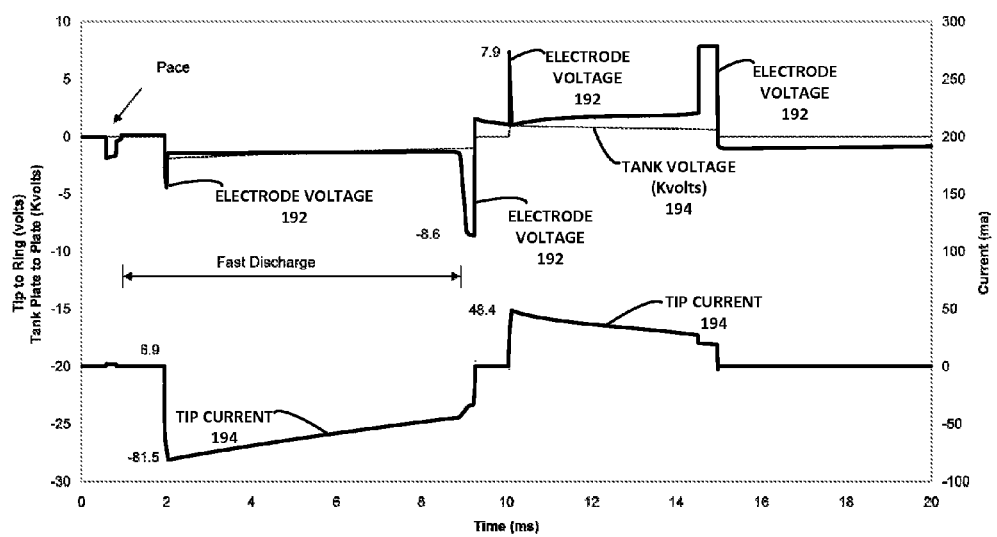

Experimental Results (FIGS. 9A-9C)

FIGS. 9A-9C illustrate examples of defibrillation pulse polarization resulting from an anti-tachyarrhythmia shock occurring on or shortly after a pacing pulse. FIGS. 9A-9C demonstrate the ability to detect an anti-tachyarrhythmia shock using defibrillation pulse polarization techniques as described with respect to defibrillation pulse polarization detector 160. During the testing represented by FIGS. 9A-9C, pacing electrodes of a cardiac stimulation device configured to perform sensing as discussed with respect to FIGS. 6A-8 were located in a saline solution with defibrillation electrodes of a separate defibrillation device. For example, the pacing electrodes may represent electrodes of LPD 16. As indicated by FIGS. 9A-9C, defibrillation pulse polarization resulted in a voltage change on sensing/pacing electrodes of at least about 1 volt.

FIG. 9A illustrates electrode voltage 172, which represents voltage across electrodes of an LPD, such as electrodes 52, 60 of LPD 16, and tank voltage 174, which represents the voltage across the defibrillation electrodes in the experimental tank. Tank voltage 174 is used to simulate an anti-tachyarrhythmia shock. FIG. 9A further illustrates tip current 176, which represents the current through the electrodes of the LPD, again simulating an anti-tachyarrhythmia shock.

Electrode voltage 172 includes spikes due to a biphasic defibrillation pulse as represented by tip current 176. Electrode voltage 172 not only represents the response to tip current 176, but also includes a pace blanking period 173. The pace blanking period 173 is coincident with a pacing pulse delivered by the LPD during a positive phase of the anti-tachyarrhythmia shock, a time with voltage amplitude or fast edge sensing may be blanked. Tank voltage 174 represents the total voltage differential across a tank holding the saline solution. The pacing pulse of FIG. 9A occurred during the second phase of the biphasic defibrillation pulse, but the spikes in electrode voltage 172 are still apparent.

FIG. 9B illustrates electrode voltage 182, which represents voltage across electrodes of an LPD, such as electrodes 52, 60 of LPD 16, and tank voltage 184, which represents the voltage across the electrodes in the experimental tank. Tank voltage 184 is used to simulate an anti-tachyarrhythmia shock. FIG. 9B further illustrates tip current 186, which represents the current through the electrodes of the LPD, again simulating an anti-tachyarrhythmia shock. The pacing pulse of FIG. 9B occurs prior to the biphasic defibrillation pulse, and the spikes in electrode voltage 182 are detectable.

Similarly, FIG. 9C illustrates electrode voltage 192, which represents voltage across electrodes of an LPD, such as electrodes 52, 60 of LPD 16, and tank voltage 194, which represents the voltage across the electrodes in the experimental tank. Tank voltage 194 is used to simulate an anti-tachyarrhythmia shock. FIG. 9C further illustrates tip current 186, which represents the current through the electrodes of the LPD, again simulating an anti-tachyarrhythmia shock. The pacing pulse of FIG. 9C occurring prior to the biphasic defibrillation pulse, and the spikes in electrode voltage 192 are detectable.

FIG. 10 illustrates an example waveform 200 of biphasic cardiac pacing, such as ATP pacing, including a pacing pulse having two windows, an initial negative discharge pacing window 202, and a subsequent positive discharge window 206, separated by a period of substantially no stimulation 204, the period of no stimulation 204 being suitable for sensing electrical signals, including electrical signals indicative of an anti-tachyarrhythmia shock. In one example, the period of no stimulation 204 may have a duration between about 1 millisecond to about 20 milliseconds. In another example, the period of no stimulation 204 may have a duration about 5 milliseconds to about 10 milliseconds. In one particular example, the period of no stimulation 204 may be about 10 milliseconds. The period of no stimulation 204 may be used to detect an anti-tachyarrhythmia shock with anti-tachyarrhythmia shock signal edge detector 140 and/or defibrillation pulse amplitude detector 150. Specifically, the period of no stimulation 204 allow for sensing with anti-tachyarrhythmia shock signal edge detector 140 and/or defibrillation pulse amplitude detector 150. This reduces the probability that an anti-tachyarrhythmia shock would fail to be detected due to blanking because one of the detectable artifacts of the resulting electrical signal should fall within the period of no stimulation 204 (where monitoring is resumed) and be detected.

FIG. 11 illustrates an example waveform 210 of biphasic cardiac pacing, such as ATP pacing, including a pacing pulse having three pacing windows and two periods of substantially no stimulation. More specifically, waveform 210 includes an initial negative discharge pacing window 212, a relatively short period of substantially no stimulation 214, and a subsequent positive discharge window 216, then a relatively long period of substantially no stimulation 215, followed by a second positive discharge window 217. The periods of no stimulation 214, 215 are suitable for sensing electrical signals, including electrical signals indicative of an anti-tachyarrhythmia shock. In one example, the period of no stimulation 214 may have a duration between about 0.2 milliseconds to about 5 milliseconds. In another example, the period of no stimulation 215 may have a duration about 1 milliseconds to about 20 milliseconds. In one particular example, the period of no stimulation 214 may be about 1 millisecond and the period of no stimulation 215 may be between about 3 millisecond to about 20 milliseconds. A period of no stimulation 214, 215 may be used to detect an anti-tachyarrhythmia shock with anti-tachyarrhythmia shock signal edge detector 140 and/or defibrillation pulse amplitude detector 150. Specifically, each period of no stimulation 214, 215 allows for sensing with anti-tachyarrhythmia shock signal edge detector 140 and/or defibrillation pulse amplitude detector 150. This reduces the probability that an anti-tachyarrhythmia shock would fail to be detected due to blanking because at least one of the detectable artifacts of the resulting electrical signal should fall within one of the periods of no stimulation (where monitoring is resumed) and be detected.

Figure 12:
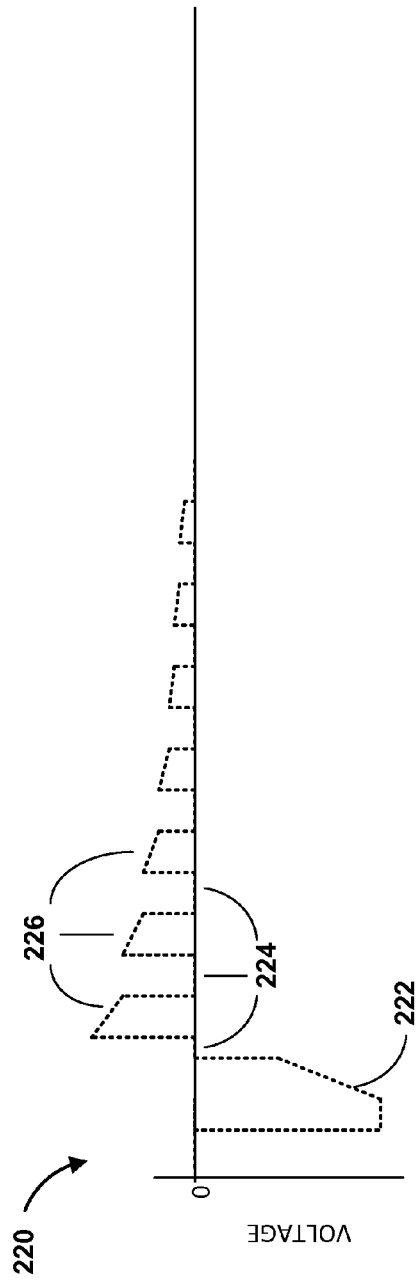
FIG. 12 illustrates an example waveform of biphasic cardiac pacing including a pacing pulse having multiple pacing windows separated by periods of substantially no stimulation, the periods of no stimulation being suitable for sensing electrical signals, including electrical signals indicative of an anti-tachyarrhythmia shock.

FIG. 12 illustrates an example waveform 220 of biphasic cardiac pacing, such as ATP pacing, including a pacing pulse having multiple windows, an initial negative discharge pacing window 222 and a series of positive discharge windows 226, each of less than about 5 milliseconds or even about 2 milliseconds. Adjacent positive discharge windows 226 are separated by periods of substantially no stimulation 224. The periods of no stimulation 224 are suitable for sensing electrical signals, including electrical signals indicative of an anti-tachyarrhythmia shock. In one example, each period of no stimulation 224 may have a duration between about 0.1 millisecond to about 20 milliseconds. In another example, a period of no stimulation 224 may have a duration about 5 milliseconds to about 10 milliseconds. In one particular example, a period of no stimulation 224 may be about 1 milliseconds. A period of no stimulation 224 may be used to detect an anti-tachyarrhythmia shock with anti-tachyarrhythmia shock signal edge detector 140 and/or defibrillation pulse amplitude detector 150. Waveform 220 allows for a short pace blanking time relative of the duration of an anti-tachyarrhythmia shock such that would be impossible to hide it completely within the blanking period. This reduces the probability that an anti-tachyarrhythmia shock would fail to be detected due to blanking because at least one of the detectable artifacts of the resulting electrical signal should fall within one of the periods of no stimulation (where monitoring is resumed) and be detected. However, pacing according to waveform 220 may leave more polarization behind following discharge pacing window 222 since the charge from the pace will not be immediately compensated for by charge from the discharge. A higher threshold for defibrillation pulse amplitude detector 150 may be required to prevent detection of the pacing pulse polarization. For example, the threshold could be boosted higher immediately after a pace pulse (twice as large for example) and then decreased gradually during the series of positive discharge windows 226 or all at once at the end of the discharge sequence.

Figure 13:
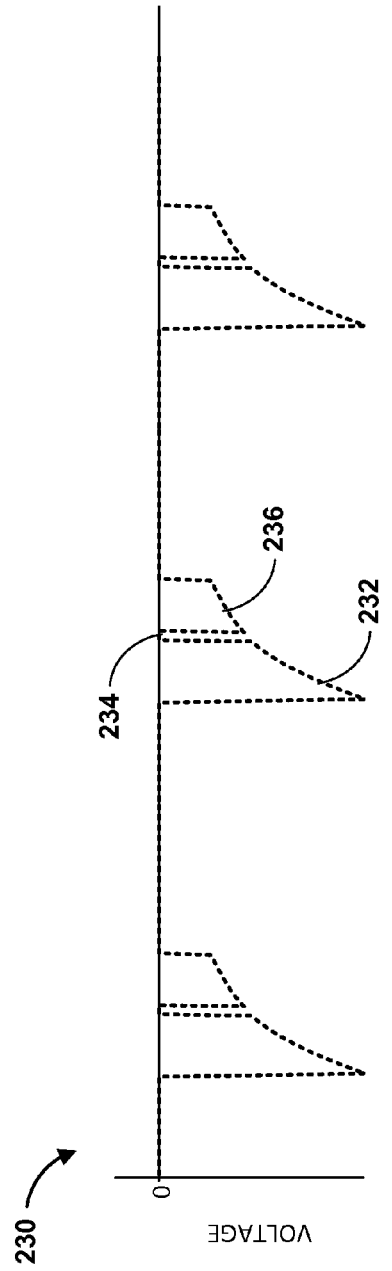
FIG. 13 illustrates an example waveform of monophasic cardiac pacing including a pacing pulse having two windows separated by a period of substantially no stimulation, the period of no stimulation being suitable for sensing electrical signals, including electrical signals indicative of an anti-tachyarrhythmia shock.

FIG. 13 illustrates an example waveform 230 of monophasic cardiac pacing, such as ATP pacing, including a pacing pulse having two windows, an initial discharge negative pacing window 232, and a subsequent negative pacing window 236, separated by a period of substantially no stimulation 234, the period of no stimulation 234 being suitable for sensing electrical signals, such including electrical signals indicative of an anti-tachyarrhythmia shock. In one example, the period of no stimulation 234 may have a duration between about 0.2 milliseconds to about 20 milliseconds. In another example, the period of no stimulation 234 may have a duration between about 5 milliseconds to about 10 milliseconds. In one particular example, the period of no stimulation 234 may be about 1 millisecond. The period of no stimulation 234 may be used to detect an anti-tachyarrhythmia shock with anti-tachyarrhythmia shock signal edge detector 140 and/or defibrillation pulse amplitude detector 150. This reduces the probability that an anti-tachyarrhythmia shock would fail to be detected due to blanking because at least one of the detectable artifacts of the resulting electrical signal should fall within the period of no stimulation (where monitoring is resumed) and be detected.

Figure 14:
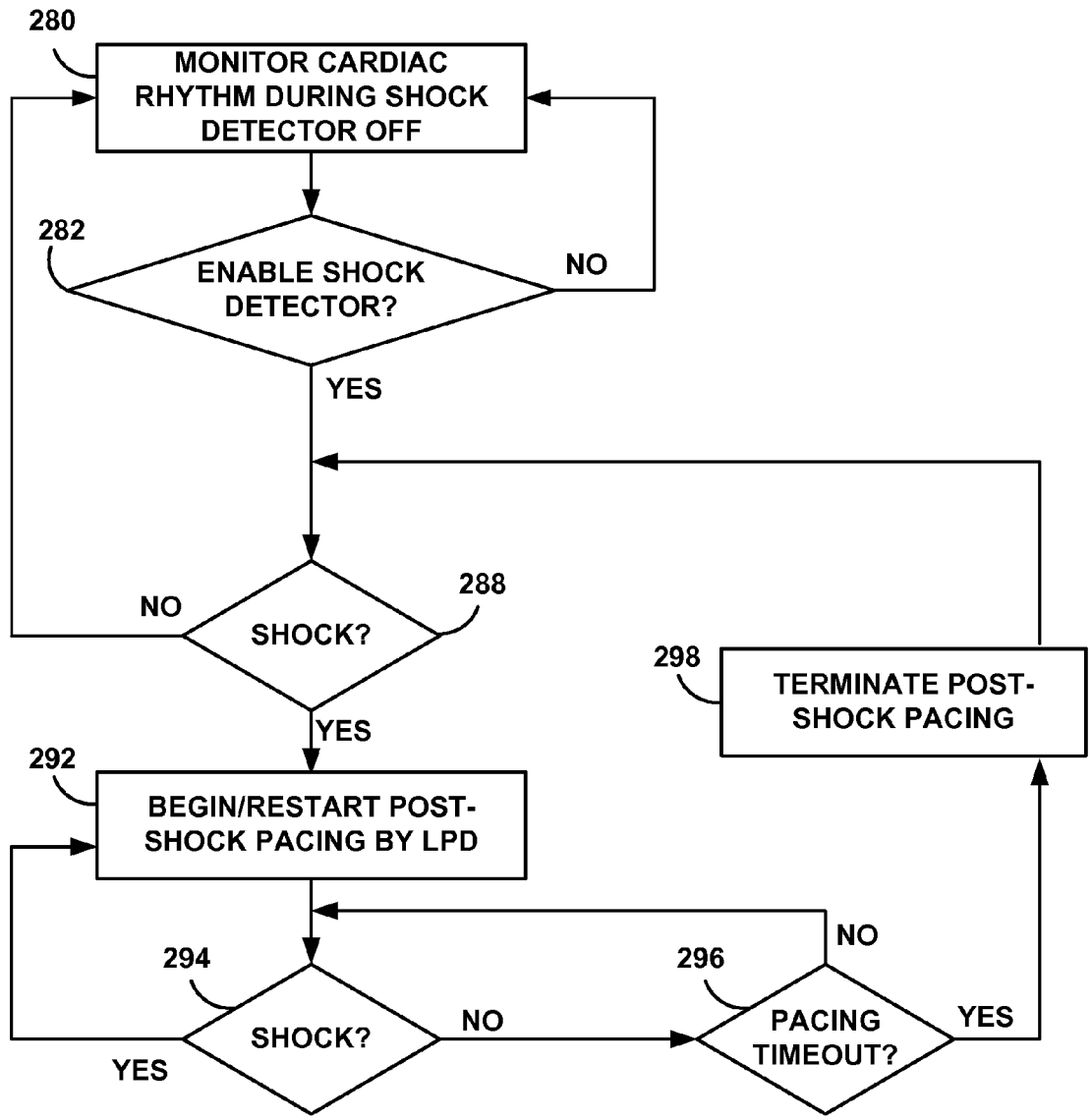
FIG. 14 is a flow diagram of an example process for detecting an anti-tachyarrhythmia shock and delivering post-shock therapy by an implantable pacing device, such as an LPD.

FIG. 14 is a flow diagram of an example process for delivering tachyarrhythmia therapy by LPD 16, which includes detecting an anti-tachyarrhythmia shock delivered by another device. The example of FIG. 14 will be described with respect to LPD 16 operating without direct communication to subcutaneous ICD system 30. In this manner, LPD 16 is capable of determining when to terminate ATP and/or initiate post-shock pacing without any instruction from another device, such as subcutaneous ICD system 30 or other internal or external defibrillation device.

As shown in FIG. 14, processor 90 of LPD 16 may monitor a cardiac rhythm from an electrical signal sensed from heart 18 (280). This monitoring may occur during a period of time when shock detector 99 is off or disabled. Disabling of shock detector 99 may reduce power consumption by LPD 16 and extend the battery life of power source 102. Therefore, processor 90 may need to enable shock detector 99 at some point during operation of LPD 16. In alternative examples, shock detector 99 may be operated continuously or periodically in a functionally continuous manner. In other alternative examples, the sense amplifier may provide an indication of a shock when the normal shock detector is disabled, and the shock detector would provide detection of a shock when it is enabled.

If processor 90 detects that the shock detector should be enabled (e.g., detect an arrhythmia eligible for anti-tachyarrhythmia shock therapy) ("YES" branch of block 282), processor 90 proceeds to enable shock detector 99. If processor 90 determines that the shock detector does not need to be enabled ("NO" branch of block 282), processor 90 may continue to monitor heart 18 for tachyarrhythmias (280).

If processor 90 determines that the shock detector does need to be enabled ("YES" branch of block 282), processor 90 may enable the shock detector 99 (288). Shock detector 99 detects the anti-tachyarrhythmia shock by measuring the voltage across the electrode inputs of the implanted device according to one or more of techniques for detection of an anti-tachyarrhythmia shock by an LPD or other device: detection of the high level of an anti-tachyarrhythmia shock, detection of a high slew rate of the leading and trailing edges, and detection of a large post-shock polarization change. Each technique looks for a different electrical signal characteristic. Shock detector 99 may combine one or more of these techniques to improve sensitivity and/or specificity. For example, the high level of an anti-tachyarrhythmia shock may be combined with one or both of the detection of a high slew rate of the leading and trailing edges, and the detection of a large post-shock polarization change.

If shock detector 99 detects a delivered shock ("YES" branch of block 288), processor 90 may begin post-shock pacing to heart 18 of patient 14 (292). Alternatively, or additionally, processor 90 may terminate ATP therapy. Processor 90 may start post-shock pacing by causing LPD 16 to enter a post-shock pacing mode. Detection of the anti-tachyarrhythmia shock may be used to abort and/or temporarily suspend the delivery of ATP and to activate post-shock pacing, such as VVI post-shock pacing. ATP may be temporarily suspended following an anti-tachyarrhythmia shock to insure that the pacing pulses will not induce another arrhythmia. Post-shock pacing may be used to insure pacing support if the patient's heart does not begin to beat normally immediately following an anti-tachyarrhythmia shock. A higher than normal amplitude and pulse width is commonly used to minimize the risk of loss of capture following an anti-tachyarrhythmia shock. A higher capture threshold may occur as a result of tissue stunning due to elevated current in the myocardial tissue from the anti-tachyarrhythmia shock delivery. A higher threshold may also occur as a result of physiological changes in the tissue resulting from lack of blood flow to the myocardium during VF. Furthermore, after an anti-tachyarrhythmia shock there can be increased polarization at the lead interface resulting in the need for a higher voltage to overcome the lead polarization.

If no shock has been detected ("NO" branch of block 288), processor 90 may check to if the enabled shock detector period has timed out. Processor 90 may track a period of time since shock detector 99 was enabled, and if the period of time exceeds a timeout threshold, processor 90 may disable shock detector 99 and continue to monitor ECGs for tachyarrhythmias (280). If the period after enabling shock detector 99 has not exceeded the timeout threshold ("NO" branch of block 290), processor 90 may continue to determine if any shocks have been detected (288).

In some examples, prior to delivering post-shock pacing, processor 90 may analyze sensed electrical signals from heart 18 to determine whether or not post-shock pacing is necessary. Processor 90 may analyze an ECG or other electrical signal to detect bradycardia and/or asystole. In response to the detection of bradycardia or asystole, processor 90 may begin post-shock pacing. Processor 90 may, in some example, determine one or more post-shock pacing parameters based on which rhythm was detected and/or characteristics of the detected rhythm. In response to not detecting bradycardia or asystole, processor 90 may withhold post-shock pacing and again look for any delivered shock (288).

After starting post-shock pacing (292), processor 90 may continue to determine if shock detector 99 detects any additional shocks from subcutaneous ICD system 30 or another device (294). If processor 90 detects another shock ("YES" branch of block 294), processor 90 may restart the post-shock pacing (292). Processor 90 may also track a period of time following the delivery, or the starting of delivery, of post-shock pacing (296). If processor 90 determines that the period of time following initial delivery of post-shock pacing does not exceed a timeout threshold ("NO" branch of block 296), processor 90 will continue to determine if another shock has been detected (294). If, however, processor 90 determines that the period of time following starting of post-shock pacing exceeds the timeout threshold ("YES" branch of block 296), processor 90 may responsively terminate post-shock pacing (298). Processor 90 may then return to determine if another shock has been detected (288) or if the shock detector should be disabled (280). In other examples, processor 90 may continue post-shock pacing for an undetermined period of time following detection of the shock. In some examples, LPD 16 may even continue post-shock pacing during subsequent shocks.

Figure 15A:
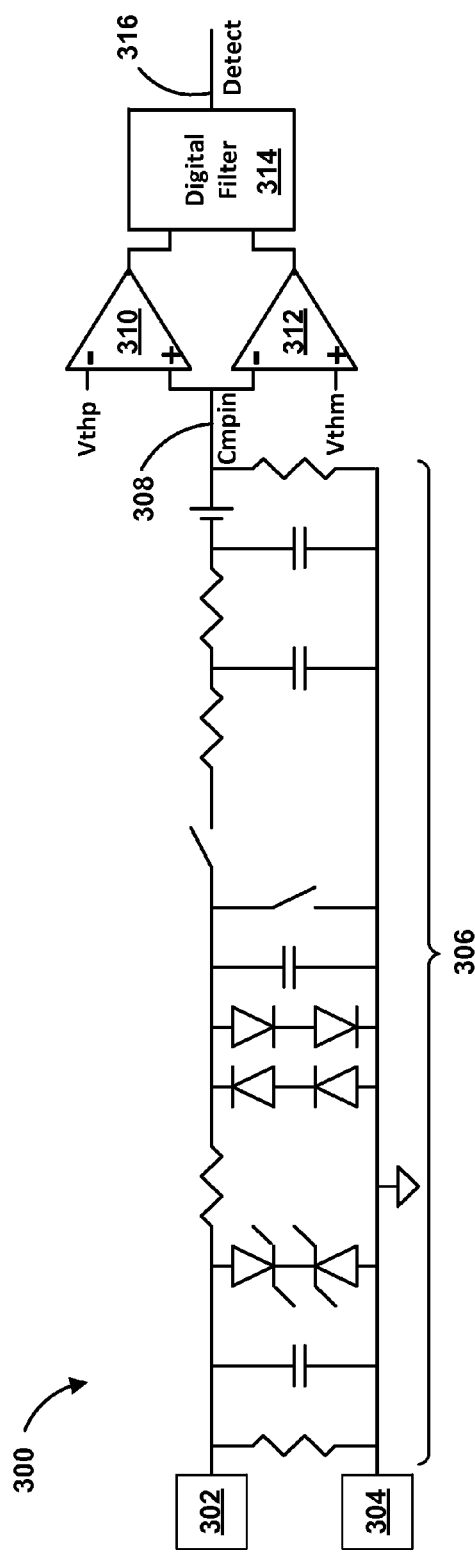
FIG. 15A illustrates an example circuit that provides analog shock signal detection suitable for inclusion as part of an anti-tachyarrhythmia shock detector.

FIG. 15A illustrates an example circuit 300 that provides analog shock signal detection suitable for inclusion as part of sensing module 98 and shock detector 99. Circuit 300 receives a voltage from LPD electrodes 302, 304. Electrode 304 is connected to ground. In one example, electrode 304 may represent a housing electrode of the IMD. Circuit 300 includes bandpass filter 306, which may be a 200 hertz to 1 kilohertz bandpass filter. Bandpass filter 306 functions to limit signal noise that may otherwise be detected as an anti-tachyarrhythmia shock, and the range of bandpass filter 306 may be selected accordingly.

Bandpass filter 306 outputs filtered signal 308 to comparators 310, 312. Comparator 310 indicates to digital filter 314 when a positive voltage has an amplitude that exceeds a predefined level Vthp, whereas comparator 312 indicates to digital filter 314 when a negative voltage has an amplitude that exceeds a predefined level Vthm. Thus, comparators 310, 312 combine detect when the magnitude of the filtered signal from bandpass filter 306 exceeds programmed threshold voltages of comparators 310, 312. Digital filter 314 receives the signals from comparators 310, 312 and outputs a digital detection signal 316 according to one or more shock detection techniques as described herein including a relatively high amplitude level of an anti-tachyarrhythmia shock, detection of a high slew rate of the leading and trailing edges, detection of a large post-shock polarization change, or any combination thereof.

In some examples, a different bandpass filter may be used in combination with bandpass filter 306 to facilitate detection of cardiac signals using digital filter 314. For example, a cardiac signal detection bandpass filter may have a range of about 20 hertz to about 70 hertz. This may allow circuit 300 to be implemented in combination with cardiac signal detection circuitry within an cardiac stimulator such as an LPD as such an implementation would only require the addition of bandpass filter 306 and comparators 310, 312 to cardiac signal detection circuitry.

Figure 15B:
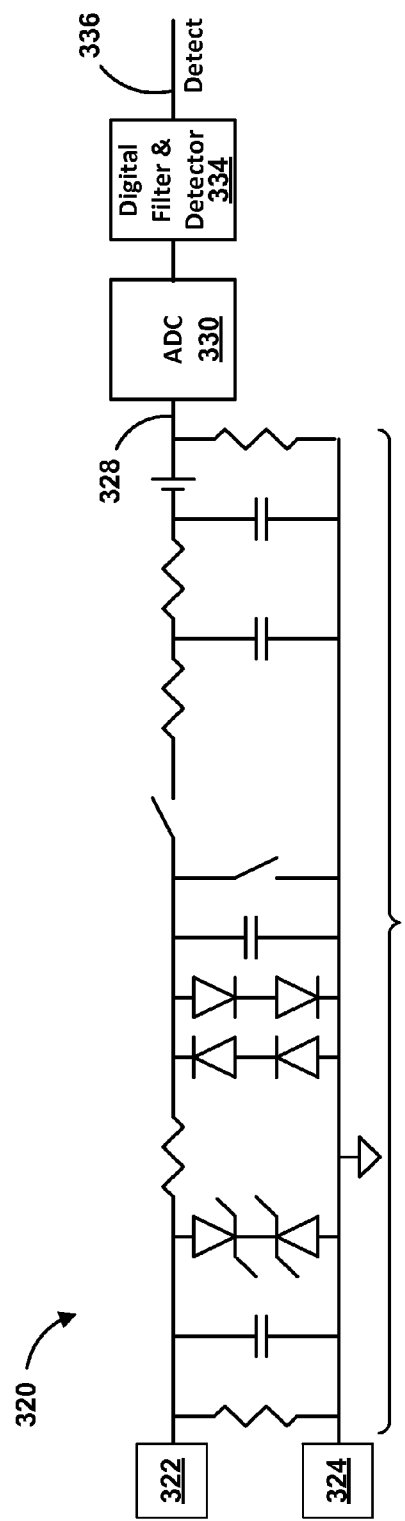
FIG. 15B illustrates an example circuit that provides digital shock signal detection suitable for inclusion as part of an anti-tachyarrhythmia shock detector.

FIG. 15B illustrates an example circuit 320 that provides digital shock signal detection suitable for inclusion as part of sensing module 98 and shock detector 99. Circuit 320 receives a voltage from LPD electrodes 322, 324. Electrode 324 is connected to ground. In one example, electrode 324 may represent a housing electrode of the IMD. Circuit 320 includes bandpass filter 326, which may be a 200 hertz to 1 kilohertz bandpass filter. Bandpass filter 326 functions to limit signal noise that may otherwise be detected as an anti-tachyarrhythmia shock, and the range of bandpass filter 326 may be selected accordingly.

Circuit 320 further includes analog to digital converter 330 to digitize the filtered input 328. Digital filter and detector 334 receives the digital signal from analog to digital converter 330 and outputs a digital detection signal 336 according to one or more anti-tachyarrhythmia shock detection techniques as described herein including a relatively high amplitude level of an anti-tachyarrhythmia shock, detection of a high slew rate of the leading and trailing edges, detection of a large post-shock polarization change, or any combination thereof.

In some examples, a different bandpass filter may be used in combination with bandpass filter 326 to facilitate detection of cardiac signals using digital filter 334. For example, a cardiac signal detection bandpass filter may have a range of about 20 hertz to about 70 hertz. This may allow circuit 320 to be implemented in combination with cardiac signal detection circuitry within an cardiac stimulator such as an LPD as such an implementation would only require the addition of bandpass filter 326 to cardiac signal detection circuitry.

Alternatively, the different filtering ranges for detection of cardiac signals as compared to detection of anti-tachyarrhythmia shock may be implemented digitally, e.g., by digital filter and detector 334. In such an example, bandpass filter 326 may provide a comparatively large range or distinct ranges to allow cardiac signals, e.g., 20 hertz to about 70 hertz, as well as anti-tachyarrhythmia shock signals, e.g., 200 hertz to 1 kilohertz, to be included in filtered signal 328 received by analog to digital converter 330.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to subcutaneous ICD system 30, LPD 16, programmer 21, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between subcutaneous ICD system 30, LPD 16 and/or programmer 21. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described for delivering cardiac stimulation and defibrillation therapies as well as coordinating the operation of separate LPDs and subcutaneous ICDs implanted within a patient. Any combination of the described operations or functions is contemplated. These and other examples are within the scope of the following claims.

What is claimed is:

1. A method for detecting, with an implantable pacemaker, delivery of an anti-tachyarrhythmia shock by another device comprising:
   delivering, by the implantable pacemaker, cardiac stimulation therapy;
   sensing, by the implantable pacemaker via an electrode pair within the patient, an electrical signal;
   detecting, by the implantable pacemaker, the anti-tachyarrhythmia shock based on the sensed electrical signal by detecting DC voltage polarization across the electrode pair within the patient; and
   altering the cardiac stimulation therapy delivered by the implantable pacemaker based on the detected anti-tachyarrhythmia shock.

2. The method of claim 1, wherein detecting the anti-tachyarrhythmia shock based on the sensed electrical signal further includes detecting an edge of the anti-tachyarrhythmia shock based on a change in voltage at or greater than a predetermined edge detection voltage amplitude threshold and over a time period of not greater than about 2 milliseconds within the sensed electrical signal.

3. The method of claim 2, wherein detecting the anti-tachyarrhythmia shock based on the sensed electrical signal further includes detecting a voltage at or greater than a predetermined amplitude threshold within the sensed electrical signal.

4. The method of claim 1, wherein detecting the anti-tachyarrhythmia shock based on the sensed electrical signal further includes detection of a change in voltage at or greater than a predetermined amplitude threshold within the sensed electrical signal.

5. The method of claim 1, further comprising delivering anti-tachycardia pacing to the heart of the patient prior to detecting the anti-tachyarrhythmia shock.

6. The method of claim 5, further comprising:
   upon detecting the anti-tachyarrhythmia shock based on the sensed electrical signal, refraining from the delivery of anti-tachycardia pacing to the heart of the patient; and
   upon detecting the anti-tachyarrhythmia shock based on the sensed electrical signal, delivering post-shock pacing therapy.

7. The method of claim 5,
   wherein the cardiac stimulation therapy includes a pacing pulse with two windows separated by a period of substantially no stimulation, the period of substantially no stimulation being between about 20 milliseconds to about 1 millisecond, and
   wherein sensing, from the electrode pair within the patient, includes sensing during the period of substantially no stimulation of the pacing pulse.

8. The method of claim 1, wherein the anti-tachyarrhythmia shock was delivered by one of:
   an implantable medical device; and
   an external medical device.

9. The method of claim 1, wherein the anti-tachyarrhythmia shock is one of:
   a defibrillation pulse; and
   a cardioversion pulse.

10. The method of claim 1, wherein delivering, by the implantable pacemaker, cardiac stimulation therapy, includes delivering the cardiac stimulation therapy via the electrode pair.

11. An implantable pacing device comprising:
    an electrode pair;
    a signal generator configured to deliver cardiac stimulation therapy to a heart of a patient;

a shock detector configured to sense, from the electrode pair when the implantable medical device is implanted within a patient, an electrical signal; and a processor configured to detect an anti-tachyarrhythmia shock based on the sensed electrical signal by detecting DC voltage polarization across the electrode pair within the patient, and alter the cardiac stimulation therapy based on the detected anti-tachyarrhythmia shock.

12. The implantable pacing device of claim 11, wherein the processor is configured to detect the anti-tachyarrhythmia shock further based on a change in voltage at or greater than a predetermined edge detection voltage amplitude threshold and over a time period of not greater than about 2 milliseconds within the sensed electrical signal.

13. The implantable pacing device of claim 11, wherein the processor is configured to detect the anti-tachyarrhythmia shock further based a change in voltage at or greater than a predetermined amplitude threshold within the sensed electrical signal.

14. The implantable pacing device of claim 11, wherein altering the cardiac stimulation therapy based on the detected anti-tachyarrhythmia shock comprises:
- upon detecting the anti-tachyarrhythmia shock based on the sensed electrical signal, refraining from the delivery of anti-tachycardia pacing; and
- upon detecting the anti-tachyarrhythmia shock based on the sensed electrical signal, delivering post-shock pacing therapy via the signal generator.

15. The implantable pacing device of claim 11, wherein the implantable pacing device is a leadless pacing device, the leadless pacing device further comprising:
- a housing configured to be implanted within the heart of the patient, the electrode pair being coupled to the housing; and
- a fixation mechanism configured to attach the housing to tissue of the heart.

16. The implantable pacing device of claim 11,
wherein the cardiac stimulation therapy includes a pacing pulse with two or more windows separated by one or more period of substantially no stimulation, the periods of substantially no stimulation being between about 0.1 milliseconds to about 20 milliseconds,
wherein the shock detector configured to sense, from the electrode pair within the patient, the electrical signal during the periods of substantially no stimulation of the pacing pulse.

17. The implantable pacing device of claim 11, wherein the signal generator is configured to deliver the cardiac stimulation therapy to the heart of the patient via the electrode pair.

18. A system comprising:
- a subcutaneous implantable cardioverter defibrillator comprising a first set of electrodes and configured to:
  - sense a first electrical signal from a heart of a patient via the one or more first electrodes;
  - detect a tachyarrhythmia within the sensed first electrical signal; and
  - determine, based on the detected tachyarrhythmia, to deliver anti-tachyarrhythmia shock therapy to the patient to treat the detected arrhythmia; and
- a leadless pacing device configured to be implanted within the heart of the patient, wherein the leadless pacing device comprises:
  - a second set of electrodes;
  - a signal generator configured to deliver stimulation therapy to the heart of the patient;
  - a shock detector configured to sense, from the second set of electrodes when the leadless pacing device is implanted within a patient, an electrical signal; and
  - a processor configured to detect an anti-tachyarrhythmia shock based on the sensed electrical signal by detecting DC voltage polarization across the second set of electrodes within the patient, and alter the cardiac stimulation therapy based on the detected anti-tachyarrhythmia shock.

19. The system of claim 18, wherein the processor is configured to detect the anti-tachyarrhythmia shock further based a change in voltage at or greater than a predetermined amplitude threshold within the sensed electrical signal.

20. The system of claim 18,
wherein the stimulation therapy includes a cardiac pacing pulse with two or more windows separated by one or more period of substantially no stimulation, the periods of substantially no stimulation being between about 0.1 milliseconds to about 20 milliseconds,
wherein the shock detector configured to sense, from the electrode pair within the patient, the electrical signal during the periods of substantially no stimulation of the pacing pulse.

* * * * *